(12) United States Patent
Hansen et al.

(10) Patent No.: US 6,531,617 B2
(45) Date of Patent: Mar. 11, 2003

(54) PROCESS FOR PREPARING HYDROXYCHOMANONES AND CIS-AMINOCHROMANOLS

(75) Inventors: Karl Hansen, Atlantic Highlands, NJ (US); Paul Devine, Lincroft, NJ (US); Philippe M. Rabbat, New York, NY (US)

(73) Assignee: Merck & Co., Inc., Rahway, NJ (US)

(*) Notice: Subject to any disclaimer, the term of this patent is extended or adjusted under 35 U.S.C. 154(b) by 52 days.

(21) Appl. No.: 10/001,369

(22) Filed: Oct. 24, 2001

(65) Prior Publication Data

US 2002/0095047 A1 Jul. 18, 2002

Related U.S. Application Data

(60) Provisional application No. 60/242,799, filed on Oct. 24, 2000.

(51) Int. Cl.⁷ .................. C07D 311/22; C07D 311/56
(52) U.S. Cl. ........................ 549/400; 549/401
(58) Field of Search ................ 549/400, 401

(56) References Cited

U.S. PATENT DOCUMENTS

| 5,413,999 | A | 5/1995 | Vacca et al. |
| 6,057,479 | A | 5/2000 | Mitamura et al. |
| 6,384,244 | B2 | 5/2002 | Davies et al. |

FOREIGN PATENT DOCUMENTS

| EP | 0 434 365 | 6/1991 |

OTHER PUBLICATIONS

S. Sethna, "Cycliacylation", Chapter XXXV, in Friedel–Crafts and Related Reactions, vol. III, part 2, Interscience, pp. 911–1002 (1964).
H. Kajiro et al., "A Practical Synthesis of (1S, 2R)–1–Amino–2–indanol, a Key Component of an HIV Protease Inhibitor, Indinavir", Bull. Chem. Soc. Jpn., vol. 72, pp. 1093–1100 (1999).
R. Bognar et al., "Stereochemistry of Flavan–3,4–Diols", Tetrahedron, vol. 19, pp. 391–394 (1963).
R. Bognar et al., "A New Method for the Preparation of 4–Hydroxyflavans", Tetrahedron Letters, No. 19, pp. 4–8 (1959).
D. R. Julian et al., "Synthesis of [1] Benzopyranol[3,4–b] [1,4] oxazines as Potential Antidepressants", J. Het. Chem., vol. 12, pp. 1179–1182 (1975).
A. K. Ghosh et al., "Stereoselective Reduction of Alpha–Hydroxy Oxime Ethers: A Convenient Route to Cis–1, 2–Amino Alcohols", Tetrahedron Letters, vol. 32, No. 6, pp. 711–714 (1991).
H. Kajiro et al., "A Practical Synthesis of (1S, 2R)–1–Amino–2–indanol, a Key Component of HIV Protease Inhibitor, Indinavir", Synlett, pp. 51–52 (Jan. 1998).
C. H. Senanayake et al., "The Role of 4–(3–Phenylpropyl)pyridine N–Oxide ($P_3NO$) in the Manganese–Salen–Catalyzed Asymmetric Epoxidation of Indene", Tetrahedron Letters, vol. 37, No. 19, pp. 3271–3274 (1996).
C. H. Senanayake et al., "The Behavior of Indene Oxide in the Ritter Reaction: A Simple Route to cis–Aminoindanol", Tetrahedron Letters, vol. 36, No. 23, pp. 3993–3996 (1995).
J. M. Ready et al., "Asymmetric Catalytic Synthesis of Alpha–Aryloxy Alcohols: Kinetic Resolution of Terminal Epoxides via Highly Enantioselective Ring–Opening with Phenols", J. Am. Chem. Soc., vol. 121, pp. 6086–6087 (1999).
K. Kabuto et al., "The Synthesis and the Stereochemistry of 4–Chromanones and 4–Chromanols with Bulky Substituents", Bull. Chem. Soc. Jpn., vol. 46, pp. 1839–1844 (1973).
B. Loubinoux et al., "Enantioselective Preparation of 2–Alkyl–3–Aryloxypropionic Acids and Esters and 3–Alkyl–4–Chromanones", Tetrahedron Letters, vol. 33, No. 16, pp. 2145–2148 (1992).
N. H. Lee et al., "Enantioselective Epoxidation of Conjugated Dienes and Enynes. Trans–Epoxides from Cis–Olefins", Tetrahedron Letters, vol. 32, No. 45, pp. 6533–6536 (1991).
A. Nemes et al., "Alternative Routes to Vincamine", Heterocycles, vol. 32, No. 12, pp. 2329–2338 (1991).
I. W. Davies et al., "Stereoselective hydrogen bromide–promoted hydrogenation of an alpha–hydroxyoxime", Tetrahedron Letters, vol. 41, pp. 8021–8025 (2000).

*Primary Examiner*—Ba K. Trinh
(74) *Attorney, Agent, or Firm*—Kenneth R. Walton; Valerie J. Camara

(57) ABSTRACT

Enantiomerically enriched hydroxychromanones are obtained by the $AlCl_3$-catalyzed intramolecular Friedel-Crafts acylation of the corresponding 3-phenoxy-2-alkylcarbonyloxy-propionic acid followed by cleavage of the carboxylate in the presence of an alkali metal peroxide or hydroperoxide. Enantiomerically enriched cis-aminochromanols can then be prepared by treating the hydroxychromanones with a hydroxylamine and hydrogenating the resulting oxime. The cis-aminochromanols can be employed as intermediates in the production of HIV protease inhibitors which are useful for treating HIV infection and AIDS.

25 Claims, No Drawings

PROCESS FOR PREPARING HYDROXYCHOMANONES AND CIS-AMINOCHROMANOLS

This application claims the priority benefit of the provisional application No. 60/242,799 dated Oct. 24, 2000.

FIELD OF THE INVENTION

The present invention relates to the preparation of enantiomerically enriched hydroxychromanones by the $AlCl_3$-catalyzed intramolecular Friedel-Crafts acylation of the corresponding 3-phenoxy-2-alkylcarbonyloxy-propionic acid followed by cleavage of the carboxylate in the presence of an alkali metal peroxide or hydroperoxide. The present invention further relates to the preparation of enantiomerically enriched cis-aminochromanols by the diastereomeric reduction of oximes derived from the hydroxychromanones. The cis-aminochromanols are useful as intermediates in the preparation of HIV protease inhibitors.

References are made throughout this application to various published documents in order to more fully describe the state of the art to which this invention pertains. The disclosures of these references are hereby incorporated by reference in their entireties.

BACKGROUND OF THE INVENTION cis-Aminochromanols are useful as intermediates in the preparation of HIV protease inhibitor compounds, which can be used to treat HIV infection, AIDS and ARC. EP 434,365 discloses, inter alia, a series of N-substituted 2(R)-((morpholinyl-ethoxy)phenylmethyl)-5(S)-((dimethylethoxycarbonyl)amino)-4(S)-hydroxy-6-phenyl-hexanamide derivatives which are useful as HIV protease inhibitors, including inhibitors prepared using cis-aminochromanol. In particular, reference is made to Example 21 of EP '365. U.S. Pat. No. 5,413,999 discloses certain N-substituted 2(R)-phenylmethyl-4(S)-hydroxy-pentaneamide derivatives which are useful as HIV protease inhibitors, including inhibitors which can be prepared from cis-aminochromanol. Reference is made, for example, to Table 1 of U.S. '999, the third entry in cols. 33–34.

The HIV protease inhibitor compounds typically have asymmetric centers, and the active form is often a particular enantiomer or diastereomer of the compound. In order to avoid a potentially complex and time-consuming resolution of the desired enantiomer or diastereomer from a mixture of optical isomers, it is desirable to prepare a relatively pure form of the active isomer directly using the appropriate optically active intermediates. Accordingly, it is also desirable to have an efficient, practical route for preparing optically enriched forms of cis-aminochromanols and also for preparing optically enriched forms of any intermediates and precursors thereof having chiral centers.

The present invention is directed to an efficient route for preparing optically enriched hydroxychromanones, the subsequent use of the hydroxychromanones for preparing optically enriched hydroxychromanone oximes, and the use of the oximes for preparing optically enriched cis-aminochromanols.

The following references are of interest as background:

Sethna, "Cycliacylation", Chapter XXXV in *Friedel-Crafts and Related Reactions,* Vol. III, part 2, Interscience, 1964, pages 911–1002, describes the formation of cyclic compounds via intramolecular Friedel-Crafts acylations, such as the formation of cyclic ketones from arylaliphatic acids.

Kajiro et al., *Bull. Chem. Soc. Jap.* 1999, 72: 1093–1100, discloses the preparation of (R)-2-hydroxy-1-indanone by the intramolecular Friedel-Crafts acylation of (R)-2-acetoxy-3-phenylpropanoic acid. Kajiro et al. further discloses the preparation of the corresponding hydroxyindanone oxime from (R)-2-hydroxy-1-indanone, and then hydrogenating the oxime in the presence of HBr and Pd black to obtain (1S,2R)-1-amino-2-indanol.

Bognar et al., *Tetrahedron* 1963, 19: 391–394, discloses the preparation of 4-amino-3-hydroxyflavan by the hydrogenation of the corresponding oxime in the presence of $PtO_2$ at atmospheric pressure in warm aqueous (80%) acetic acid. Bognar et al., *Tet. Letters* 1959, No. 19: 4–8, has a similar disclosure.

Julian et al., *J. Het. Chem.* 1975, 12: 1179–1182, discloses the preparation of cis-4-aminochroman-3-ol by reaction of 2-oxo-1,3a,4,9b-tetrahydro-2H[1]benzo-pyrano[4,3-d]oxazole with methanolic potassium hydroxide. EP 434,365 discloses substantially the same preparation in Example 21, Steps A and B.

Ghosh et al., *Tet. Letters* 1991, 32: 711–714, discloses the preparation of 4-aminothiochroman-3-ol by the reduction of the corresponding α-hydroxy benzyloxime with borane in tetrahydrofuran. It is further disclosed that borane reduction of an equilibrium mixture (3:2) of the anti and syn oximes afforded a 90/10 mixture of the cis/trans 4-aminothiochroman-3-ols.

U.S. Pat. No. 6,057,479 (Mitamura et al.) discloses the preparation of cis-1-amino-2-indanol by the catalytic hydrogenation of 2-hydroxy-1-indanone oxime in methanol. Example 21 of U.S. '479 discloses the hydrogenation in the presence of Pd black and HCl to give an aminoindanol product having a cis/trans selectivity of 95.5:4.5. Examples 22–23 report similar results for analogous hydrogenations using Pd/C and Pd/alumina. Example 24 discloses an analogous hydrogenation using Pd black and aqueous HBr to provide 1-amino-2-indanol product with a cis/trans ratio of 95.6:4.4. Results substantially the same as in Example 24 are also reported in Kajiro et al., *SYNLETT* 1998, p. 51.

SUMMARY OF THE INVENTION

The present invention is directed to an efficient process for preparing enantiomerically enriched 3-hydroxychroman-4-ones via the intramolecular Friedel-Crafts acylation of the corresponding 3-phenoxy-2-alkylcarbonyloxy-propionic acid followed by cleavage of the carboxylate group in the presence of an alkali metal peroxide or hydroperoxide. More particularly, the present invention is a process for preparing a hydroxychromanone of Formula (I):

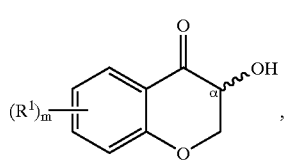

which comprises:
(C) adding an acid halide of Formula (II-C):

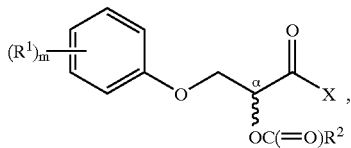
(II-C)

to a solution of $AlCl_3$ in a first organic solvent at a temperature of less than about 0° C. to form an alkylcarbonyloxy chromanone of Formula (III):

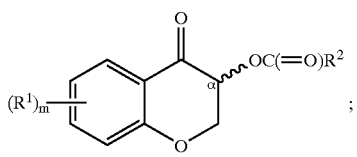
(III)

and
(D) reacting Compound III with an alkali metal peroxide or hydroperoxide in a second organic solvent at a temperature of less than about 0° C. to form Compound I;
wherein:
stereocenter α is in the R configuration or the S configuration;
each $R^1$ is independently halo, $C_1$–$C_6$ alkyl, halogenated $C_1$–$C_6$ alkyl, $C_1$–$C_6$ alkoxy, halogenated $C_1$–$C_6$ alkoxy, —$CO_2R^a$, —$COR^a$, —$NR^aR^b$, —$NR^a$—$COR^b$, —$NR^a$—$CO_2R^b$, —CO—$NR^aR^b$, —OCO—$NR^aR^b$, —$NR^aCO$—$NR^aR^b$, —$S(O)_p$—$R^a$, wherein p is an integer from 0 to 2, —$S(O)_2$—$NR^aR^b$, —$NR^aS(O)_2$—$R^b$, or —$NR^aS(O)_2$—$NR^aR^b$;
$R^2$ is $C_1$–$C_6$ alkyl;
X is halo;
each $R^a$ and $R^b$ is independently hydrogen, $C_1$–$C_4$ alkyl, or $(CH_2)_{0-3}CF_3$; and
m is an integer from 0 to 4.

The process of the invention can be conducted with the occurrence of little or no racemization. It has unexpectedly been found that the order of addition of the reactants and the reaction temperature in Step C of the process of the invention are key factors for minimizing racemization. More particularly, processes essentially the same as the process of the invention except that (i) $AlCl_3$ is added to a solution of the acid halide (versus addition of acid halide to an $AlCl_3$ solution) and/or (ii) the acylation is conducted at a temperature above 0° C. (versus temperatures below 0° C.) will typically afford a hydroxychromanone product having a comparatively much higher degree of racemization and a greater loss of enantiomeric excess. It has also unexpectedly been found that the use of an alkali metal peroxide or hydroperoxide (e.g., LiOOH) and low temperatures in the Step D carboxylate cleavage (e.g., deacetylation) is important for minimizing product racemization; i.e., processes which are the same as the process of the invention except for the use of reagents other than akali metal (hydro)peroxides for the cleavage of the carboxylate (e.g., strong acids such as sulfuric acid and hydrochloric acid) and/or a higher reaction temperature will typically result in a hydroxychromanone product having much greater racemization.

The present invention also includes a process for preparing an aminochromanol of Formula (VII):

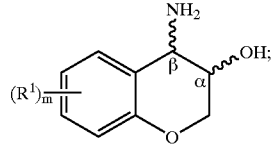
(VII)

in which the stereocenters α and β are either both in the R configuration or both in the S configuration, wherein the process comprises Steps C and D for preparing hydroxychromanone I as defined and described above, and further comprises
(E) treating hydroxychromanone I with a hydroxylamine of Formula (V):

$H_2N$—$OR^3$ (V), or an acid salt thereof, to form an oxime of Formula (VI):

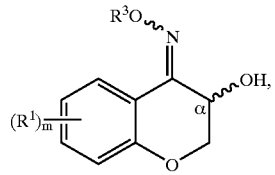
(VI)

wherein $R^3$ is
(1) hydrogen;
(2) $C_1$–$C_6$ alkyl;
(3) $C_1$–$C_6$ alkyl substituted with one or more substituents, each of which is independently halo, cyano, $C_1$–$C_4$ alkoxy, $C_1$–$C_4$ haloalkoxy, $C_3$–$C_8$ cycloalkyl, or phenyl;
(4) $C_3$–$C_8$ cycloalkyl;
(5) $C_3$–$C_8$ cycloalkyl substituted with one or more substituents, each of which is independently halo, cyano, $C_1$–$C_4$ alkyl, $C_1$–$C_4$ haloalkyl, $C_1$–$C_4$ alkoxy, $C_1$–$C_4$ haloalkoxy, or phenyl;
(6) phenyl; or
(7) phenyl substituted with one or more substituents, each of which is independently $C_1$–$C_4$ alkyl, $C_1$–$C_4$ haloalkyl, $C_1$–$C_4$ alkoxy, $C_1$–$C_4$ haloalkoxy, cyano, or halo; and
(F) hydrogenating in the presence of a palladium catalyst a mixture comprising Compound VI, a third organic solvent, and HBr to form an aminochromanol of Formula (VII).

It has been found that the mixture of E and Z oximes resulting from Step E can be hydrogenated in Step F to provide a relatively high yield of aminochromanol with high cis over trans selectivity. Hydrogenation processes similar to Step F, except for the substitution of HBr with another acid reagent and/or the substitution of Pd with another hydrogenation catalyst, have typically been found to have lower aminochromanol yields and/or lower cis/trans selectivities. Overall, the process constitutes an efficient method for synthesizing cis-aminochromanol in an enantiomerically enriched form using inexpensive and readily available starting materials.

Other embodiments, aspects and features of the present invention are either further described in or will be apparent from the ensuing description, examples and appended claims.

DETAILED DESCRIPTION OF THE INVENTION

The present invention includes a process for preparing enantiomerically enriched 3-hydroxychroman-4-ones via the intramolecular Friedel-Crafts acylation of the corresponding 3-phenoxy-2-alkylcarbonyloxy-propionic acid (e.g., 3-phenoxy-2-acetoxy-propionic acid) followed by cleavage of the carboxylate group (e.g., deacetylation) in the presence of an alkali metal peroxide or hydroperoxide (e.g., LiOOH). This process is set forth in the Summary of the Invention as Steps C and D. In one embodiment, the present invention is a process for preparing a hydroxychromanone of Formula (I*):

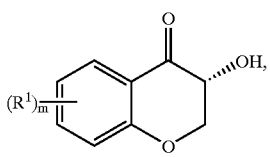
(I*)

which comprises:

(C) adding an acid halide of Formula (II-C*):

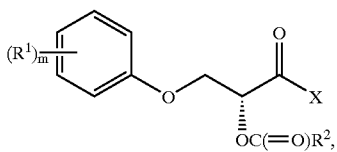
(II-C*)

to a solution of $AlCl_3$ in a first organic solvent at a temperature of less than about 0° C. to form an alkylcarbonyloxy chromanone of Formula (III*):

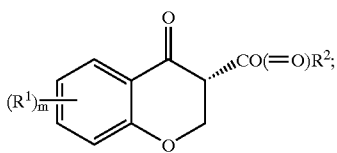
(III*)

and (D) reacting Compound III* with an alkali metal peroxide or hydroperoxide in a second organic solvent at a temperature of less than about 0° C. to form Compound I*;

wherein $R^1$, $R^2$, X and m are as defined above.

In this process, each group $R^1$ in the definition of Compounds I, II-C, and III is independently halo, $C_1$–$C_6$ alkyl, halogenated $C_1$–$C_6$ alkyl, $C_1$–$C_6$ alkoxy, halogenated $C_1$–$C_6$ alkoxy, —$CO_2R^a$, —$COR^a$, —$NR^aR^b$, —$NR^a13\ COR^b$, —$NR^a$—$CO_2R^b$, —CO—$NR^aR^b$, —OCO—$NR^aR^b$, —$NR^aCO$—$NR^aR^b$, —$S(O)_p$—$R^a$, wherein p is an integer from 0 to 2, —$S(O)_2$—$NR^aR^b$, —$NR^aS(O)_2$—$R^b$, or —$NR^aS(O)_2$—$NR^aR^b$. In one embodiment, each $R^1$ is independently halo, $C_1$–$C_6$ alkyl, halogenated $C_1$–$C_6$ alkyl, $C_1$–$C_6$ alkoxy, or halogenated $C_1$–$C_6$ alkoxy. In another embodiment, each $R^1$ is independently halo, $C_1$–$C_4$ alkyl, halogenated $C_1$–$C_4$ alkyl, $C_1$–$C_4$ alkoxy, or alogenated $C_1$–$C_4$ alkoxy. In still another embodiment, each $R^1$ is independently chloro, fluoro, $C_1$–$C_4$ alkyl, fluorinated $C_1$–$C_4$ alkyl, $C_1$–$C_4$ alkoxy, or fluorinated $C_1$–$C_4$ alkoxy. In still another embodiment, each $R^1$ is fluoro, $C_1$–$C_4$ alkyl, $(CH_2)_{0-3}CF_3$, $C_1$–$C_4$ alkoxy, or $O(CH_2)_{0-3}CF_3$. In yet another embodiment, each $R^1$ is independently fluoro, methyl, ethyl, trifluoromethyl, 2,2,2-trifluoroethyl, methoxy, ethoxy, trifluoromethoxy, or 2,2,2-trifluoroethoxy.

In the definition of $R^1$, each $R^a$ and $R^b$ is independently hydrogen, $C_1$–$C_4$ alkyl, or $(CH_2)_{0-3}CF_3$. In one embodiment, each $R^a$ and $R^b$ is independently hydrogen, methyl, ethyl, or $CF_3$.

The integer m defines the number of $R^1$ groups which may be present in Compounds I, II-C, and III, and has a value in the range of from 0 to 4. In other embodiments, m is 0 to 3; or is 1 to 3; or is 0 to 2; or is 1 to 2; or is 0 to 1; or is 0.

The group $R^2$ in the definition of Compound II-C and III is $C_1$–$C_6$ alkyl. In one embodiment, $R^2$ is $C_1$–$C_4$ alkyl. In other embodiments, $R^2$ is methyl or ethyl; or is ethyl; or is methyl.

The group X in the definition of Compound II-C is halo. In one embodiment, X is chloro, bromo, or iodo. In other embodiments, X is chloro or bromo; or is bromo; or is chloro.

In Step C acid halide II-C is added to a solution of $AlCl_3$. The solution of $AlCl_3$ can be prepared by dissolving $AlCl_3$ in an organic solvent, typically under an inert atmosphere (e.g., nitrogen or a noble gas such as argon). Suitable organic solvents include halogenated hydrocarbons selected from the group consisting of $C_1$–$C_6$ linear and branched halogenated alkanes, $C_2$–$C_6$ linear and branched halogenated alkenes, $C_5$–$C_7$ halogenated cycloalkanes, and $C_6$–$C_{10}$ halogenated aromatic hydrocarbons. Exemplary solvents include carbon tetrachloride, chloroform, methylene chloride, 1,2-dichloroethane (DCE), 1,1,2-trichloroethane (TCE), 1,1,2,2-tetrachloroethane, chlorocyclohexane, benzyl chloride, benzyl bromide, chloro- and bromo-benzene, and chloro- and bromo-toluenes. In one embodiment, the solvent is a $C_1$–$C_4$ linear or branched halogenated alkane. In an aspect of the preceding embodiment, the solvent is methylene chloride.

Prior to addition of acid halide II-C, the $AlCl_3$ solution is cooled to a temperature of less than about 0° C. The acid halide is added to the $AlCl_3$ solution while maintaining the temperature at or below about 0° C. The acid halide can be added as a solid, but is more typically added in solution form using, e.g., the same solvent used in the $AlCl_3$ solution (e.g., methylene chloride). The acid halide II-$AlCl_3$-solvent mixture is maintained at a temperature at or below about 0° C. until the desired degree of conversion has been obtained, after which the reaction can be quenched by addition of an aqueous strong acid.

The temperature in Step C is typically in a range of from about −40 to about 0° C., and is more typically in a range of from about −20 to about 0° C. (e.g., from about −20 to about −5° C.).

Any amount of $AlCl_3$ can be employed in Step C which results in the formation of at least some of Compound III. Of course, the maximum conversion of Compound II-C and maximum yield of Compound III is normally desired, and relative proportions of reactants and reagents suitable for this purpose are typically employed. $AlCl_3$ can be employed in an amount of at least about 0.1 equivalent per equivalent of Compound II-C, and is typically employed in an amount of at least about 0.5 equivalent per equivalent of Compound II-C. In one embodiment, $AlCl_3$ is employed in an amount in the range of from about 0.5 to about 5 equivalents per equivalent of Compound II-C. In another embodiment, the amount of $AlCl_3$ is in the range of from about 2 to about 3 equivalents per equivalent of II-C.

Step D involves the cleavage of the alkylcarbonyloxy group in Compound III with an alkali metal (hydro)peroxide in organic solvent to afford hydroxychromanone I. Suitable organic solvents for Step D include those selected from the group consisting of dialkyl ethers wherein each alkyl is independently a $C_1$–$C_6$ alkyl, $C_4$–$C_8$ dialkoxyalkanes, $C_4$–$C_6$ cyclic ethers and diethers, $C_6$–$C_8$ aromatic ethers, and $C_1$–$C_6$ alkyl alcohols. Exemplary solvents include ethyl ether, MTBE, THF, dioxane, 1,2-dimethoxyethane (DME), anisole, phenetole, methanol, ethanol, n- and iso-propanol, and tert-butyl alcohol. In one embodiment, the solvent is selected from the group consisting of dialkyl ethers wherein each alkyl is independently a $C_1$–$C_4$ alkyl, $C_4$–$C_6$ cyclic ethers and diethers, and $C_1$–$C_4$ alkyl alcohols. In an aspect of the preceding embodiment, the solvent is a dialkyl ether or a cyclic ether. In another aspect of the preceding embodiment, the solvent is THF.

The alkali metal (hydro)peroxide can be the peroxide or hydroperoxide of any of the alkali metals, but is typically lithium peroxide or lithium hydroperoxide. In one embodiment, the alkali metal (hydro)peroxide is LiOOH. The alkali metal (hydro)peroxide can be prepared by reacting an alkali metal basic salt (e.g., a hydroxide such as LiOH) with hydrogen peroxide in a ratio of at least one equivalent of peroxide per equivalent of alkali metal. Alkali metal peroxide (e.g., LiOOH) can be obtained, for example, by admixing the corresponding metal hydroxide (1 equivalent) dispersed or suspended in an ether solvent (e.g., THF) with aqueous $H_2O_2$ (1 equivalent).

Any amount of the (hydro)peroxide can be employed in Step D which results in the formation of at least some of Compound I. Of course, the maximum conversion of Compound III and maximum yield of Compound I is normally desired, and relative proportions of (hydro)peroxide and Compound III suitable for this purpose are typically employed. The (hydro)peroxide can be employed in an amount of at least about 0.5 equivalent per equivalent of Compound II, and is typically employed in an amount of at least about 1 equivalent per equivalent of Compound III. In one embodiment, the (hydro)peroxide is employed in an amount in the range of from about 1 to about 5 equivalents per equivalent of Compound III. In another embodiment, the amount of (hydro)peroxide is in the range of from about 1 to about 3 equivalents per equivalent of III.

Step D is suitably conducted at a temperature at or below about –0° C., and is typically conducted at a temperature in the range of from about 40 to about 0° C. In one embodiment, the temperature is in the range of from about –20 to about 0° C. (e.g., from about –20 to about –5° C.).

The reaction of Step D can be conducted by cooling a solution or suspension of the alkali metal (hydro)peroxide in suitable solvent (e.g., an ether such as THF) to the desired temperature at or below about 0° C., followed by the slow addition of a solution of Compound III in the same solvent. The mixture can then be maintained at low temperature until the desired degree of conversion is obtained, after which the reaction can be quenched (e.g., by addition of an aqueous solution of sodium bisulfite).

The products of Steps C and D (i.e., Compounds III and I respectively) can be recovered from their respective reaction mixtures at the conclusion of the reaction by conventional means; e.g., isolation from the quenched reaction mixtures using conventional techniques such as solvent extraction, chromatography, or distillation.

Another embodiment of the present invention is a process for preparing hydroxychromanone I via Steps C and D as heretofore described, which further comprises:

(B) treating a compound of Formula (II-B):

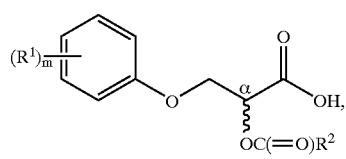

(II-B)

with an acyl halide reagent to form Compound II-C, wherein α, $R^1$ and $R^2$ are as defined above.

An aspect of the preceding embodiment is a process for preparing hydroxychromanone I* via Steps C and D as heretofore described, which further comprises:

(B) treating a compound of Formula (II-B*):

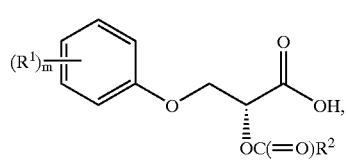

(II-B*)

with an acyl halide reagent to form Compound II-C*, wherein α, $R^1$ and $R^2$ are as defined above.

Suitable acyl halide reagents include $PCl_3$, $PCl_5$, $PBr_3$, $PBr_5$, $SOCl_2$, oxalyl chloride, and oxalyl bromide. Step B is typically conducted in an aprotic organic solvent such as a solvent selected from the group consisting of $C_3$–$C_{12}$ linear and branched alkanes, $C_1$–$C_6$ linear and branched halogenated alkanes, $C_5$–$C_7$ cycloalkanes and halogenated derivatives thereof, $C_6$–$C_{10}$ aromatic hydrocarbons and halogenated derivatives thereof, dialkyl ethers wherein each alkyl is independently a $C_1$–$C_6$ alkyl, $C_4$–$C_8$ dialkoxyalkanes, $C_4$–$C_6$ cyclic ethers and diethers, $C_6$–$C_8$ aromatic ethers. Examples of such solvents are set forth above in the description of the suitable solvents for Steps C and/or D. In one embodiment, the solvent is a $C_1$–$C_4$ linear or branched halogenated alkane. In an aspect of the preceding embodiment, the solvent is methylene chloride.

Step B is suitably conducted at a temperature in a range of from about 0 to about 60° C., and is typically conducted at a temperature of from about 5 to about 40° C.

Any amount of acyl halide reagent can be employed in Step B which results in the formation of at least some of Compound II-C. Of course, the maximum conversion of Compound II-B and maximum yield of Compound II-C is normally desired, and relative proportions of reagent and Compound II-B suitable for this purpose are typically employed. The acyl halide reagent can be employed in an amount of at least about 0.5 equivalent per equivalent of Compound II-B, and is typically employed in an amount of at least about 1 equivalent per equivalent of Compound II-B. In one embodiment, the reagent is employed in an amount in the range of from about 1 to about 3 equivalents per equivalent of Compound II-B.

The reaction of Step B can optionally be conducted in the presence of a catalytic amount of an amide including the dialkyl carboxylic acid amides (e.g., dimethylformamide and dimethylacetamide), and NMP. In one embodiment, an amide is present in an amount of at least about 0.01 equivalent per equivalent of Compound II-B. In another embodiment, an amide is present in an amount in a range of from about 0.05 to about 0.5 equivalent per equivalent of Compound II-B.

The reaction of Step B can be conducted by adding the acyl halide reagent (e.g., oxalyl chloride) to a solution of the acid II-B in an aprotic organic solvent, optionally followed by the addition of the amide. The resulting mixture can then be agitated (e.g., stirred) at reaction temperature until the desired degree of conversion is obtained. Product II-C can be recovered from the reaction mixture by conventional means.

Another embodiment of the present invention is a process for preparing hydroxychromanone I via Steps B, C and D as described above, which further comprises:

(A) treating a compound of Formula (II-A):

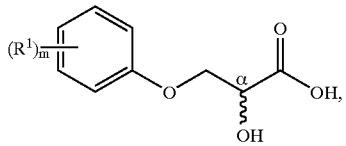
(II-A)

with an acylating agent of Formula (IV):

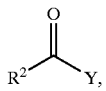
(IV)

in the absence of base, to form Compound II-B;
wherein Y is halo;
and α, m, $R^1$ and $R^2$ are as already defined.

An aspect of the preceding embodiment is a process for preparing hydroxychromanone I* via Steps B, C and D as described above, which further comprises:

(A) treating a compound of Formula (I-A*):

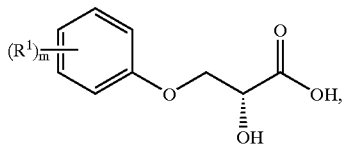
(II-A*)

with an acylating agent of Formula (IV):

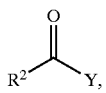
(IV)

in the absence of base, to form Compound II-B*;
wherein m, $R^1$, $R^2$ and Y are as already defined.

In one embodiment of Step A, Y is chloro, bromo, or iodo. In other embodiments, Y is chloro or bromo; or is bromo; or is chloro. Exemplary acylating agents include the acetyl chloride, acetyl bromide, propionyl chloride, propionyl bromide, butyryl chloride, isobutyryl chloride, valeryl chloride, and isovaleryl chloride. In one embodiment, the acylating agent is acetyl chloride; i.e., $R^2$ is methyl and Y is chloro.

Step A is typically conducted in a solvent selected from $C_1$–$C_6$ linear and branched halogenated alkanes, $C_5$–$C_7$ cycloalkanes and halogenated derivatives thereof, $C_6$–$C_{10}$ aromatic hydrocarbons and halogenated derivatives thereof, dialkyl ethers wherein each alkyl is independently a $C_1$–$C_6$ alkyl, $C_4$–$C_8$ dialkoxyalkanes, $C_4$–$C_6$ cyclic ethers and diethers, and $C_6$–$C_8$ aromatic ethers. Examples of such solvents are set forth above in the description of the suitable solvents for Steps C and/or D. In one embodiment, the solvent is a dialkyl ether. In an aspect of the preceding embodiment, the solvent is MTBE.

Step A is suitably conducted at a temperature in a range of from about 40° C. to reflux, and is typically conducted at a temperature of from about 50° C. to reflux. The reflux temperature of the mixture will of course depend upon the choice and relative amounts of the acylating agent, Compound II-A, and solvent.

Any amount of acylating agent can be employed in Step A which results in the formation of at least some of Compound II-B. Of course, the maximum conversion of Compound II-A and maximum yield of Compound II-B is normally desired, and relative proportions of acylating agent and Compound II-A suitable for this purpose are typically employed. The acylating agent can be employed in an amount of at least about 1 equivalent (e.g., from about 1 to about 20 equivalents) per equivalent of Compound II-A, and is typically employed in an amount of at least about 2 equivalents (e.g., from about 2 to about 10 equivalents) per equivalent of Compound II-A. In one embodiment, the reagent is employed in an amount of at least about 5 equivalents (e.g., from about 5 to about 10 equivalents) per equivalent of Compound II-A.

The reaction of Step A can be conducted by adding acylating agent (e.g., acetyl chloride) to a solution or suspension of the hydroxyacid II-A in solvent, and then heating the mixture to reflux. The mixture can then be maintained at reflux until the desired degree of conversion is obtained, optionally with periodic addition of additional portions of acylating agent. Product II-B can be recovered from the reaction mixture by conventional means (e.g., by cooling the reaction mixture and concentrating via heat or vacuum distillation).

The present invention also includes a process for preparing an oxime of Formula (VI) which comprises Steps C and D (and optionally Step B or both Steps A and B) as described above, and further comprises:

(E) treating Compound I with a hydroxylamine of Formula (V):

(V), or an acid salt thereof, to form an oxime of Formula (VI):

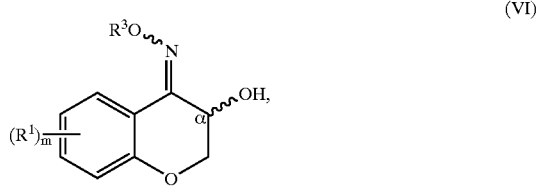
(VI)

wherein $R^3$ is
(1) hydrogen;
(2) $C_1$–$C_6$ alkyl;
(3) $C_1$–$C_6$ alkyl substituted with one or more substituents, each of which is independently halo, cyano, $C_1$–$C_4$ alkoxy, $C_1$–$C_4$ haloalkoxy, $C_3$–$C_8$ cycloalkyl, or phenyl;
(4) $C_3$–CS cycloalkyl;
(5) $C_3$–$C_8$ cycloalkyl substituted with one or more substituents, each of which is independently halo, cyano, $C_1$–$C_4$ alkyl, $C_1$–$C_4$ haloalkyl, $C_1$–$C_4$ alkoxy, $C_1$–$C_4$ haloalkoxy, or phenyl;

(6) phenyl; or (7) phenyl substituted with one or more substituents, each of which is independently $C_1$–$C_4$ alkyl, $C_1$–$C_4$ haloalkyl, $C_1$–$C_4$ alkoxy, $C_1$–$C_4$ haloalkoxy, cyano, or halo; and α, $R^1$ and m are as already defined above.

An aspect of the preceding embodiment is a process for preparing an oxime of Formula (VI*) which comprises Steps C and D (and optionally Step B or both Steps A and B) as described above, and further comprises:

(E) treating Compound I with a hydroxylamine of Formula (V):

$$H_2N-OR^3 \quad (V),$$

or an acid salt thereof, to form an oxime of Formula (VI*):

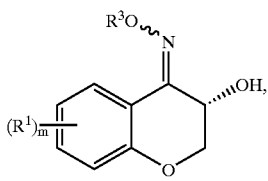

(VI*)

wherein α, $R^1$, $R^3$ and m are as already defined above.

In an embodiment of Step E, $R^3$ in the definition of Compounds V and VI is (1) hydrogen; (2) $C_1$–$C_4$ alkyl; or (3) $C_1$–$C_4$ alkyl substituted with one or more substituents, each of which is independently halo, cyano, $C_1$–$C_4$ alkoxy, $C_1$–$C_4$ haloalkoxy, $C_3$–$C_8$ cycloalkyl or phenyl. In other embodiments, $R^3$ is hydrogen, methyl, ethyl, phenyl, or benzyl; or is hydrogen.

Hydroxylamine V can be employed in Step E as a free base or more typically as an acid salt. Suitable salts include salts of mineral acids such as sulfate salts and hydrohalide salts. In one embodiment, Compound V is the sulfate salt (e.g., hydroxylamine sulfate). In another embodiment, Compound V is hydroxylamine, methoxylarmine, or benzyloxylamine, or a sulfate or hydrochloride salt thereof. In an aspect of the preceding embodiment, Compound V is the sulfate salt of hydroxylamine.

The reaction is typically conducted in a polar organic solvent such as an ether or an alcohol optionally in admixture with water as a co-solvent. Suitable ethers and alcohols include the dialkyl and aromatic ethers, dialkoxyalkanes, cyclic ethers and diethers, and aliphatic alcohols described and defined above for other process steps. The water can comprise from about 5 to about 95 volume percent based on the total volume of solvent, but the amount of water is typically in the range of from about 10 to about 50 volume percent. When an aqueous system is employed, a buffering salt such as sodium acetate is typically employed as well.

Step E is suitably conducted at a temperature in a range of from about 5° C. to about 40° C., and is typically conducted at a temperature of from about 10 to bout 40° C. In one embodiment, the reaction temperature is in a range of from about 15 to about 30° C. (e.g., from about 15 to about 25° C.).

Any amount of hydroxylamine V can be employed in Step E which results in the formation of at least some of oxime VI. Of course, the maximum conversion of hydroxychromanone I and maximum yield of oxime VI is normally desired, and relative proportions of Compounds I and V for this purpose are typically employed. The hydroxylamine V can be employed in an amount of at least about 1 equivalent (e.g., from about 1 to about 10 equivalents) per equivalent of Compound I, and is typically employed in an amount of at least about 2 equivalents (e.g., from about 2 to about 5 equivalents) per equivalent of Compound I.

The reaction of Step E can be conducted by adding hydroxylamine V, water, and optionally buffer (e.g., NaOAc) to a solution or suspension of the hydroxychromanone I in a polar solvent (e.g., THF), and then agitating (e.g., stirring) the two-phase mixture at a controlled temperature (e.g., room temperature=about 25° C.) until the desired degree of conversion is obtained. The oxime product can be recovered by separating the layers, washing and drying the organic layer, and then filtering and concentrating the organic layer. The oxime product is typically a mixture of the E and Z geometrical isomers, both of which consisting substantially of the 3(R) hydroxy optical isomer.

The present invention also includes a process for preparing an aminochromanol of Formula (VII) which comprises Steps C, D and E (and optionally Step B or both Steps A and B) as described above, and further comprises:

(F) hydrogenating in the presence of a palladium catalyst a mixture comprising Compound VI, a third organic solvent, and HBr to form an aminochromanol of Formula (VII):

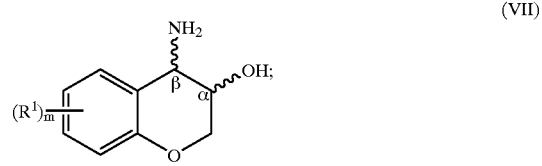

(VII)

wherein stereocenters α and β are either both in the R configuration or both in the S configuration, and $R^1$ and m are as already defined above.

An embodiment of this process is a process for preparing an aminochromanol of Formula (VII*) which comprises Steps C, D and E (and optionally Step B or both Steps A and B) as described above, and further comprises:

(F) hydrogenating in the presence of a palladium catalyst a mixture comprising Compound VI*, a third organic solvent, and HBr to form an aminochromanol of Formula (VII*):

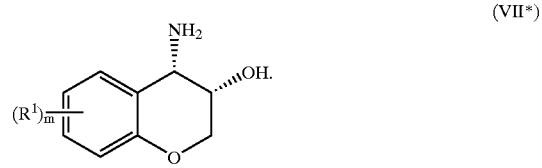

(VII*)

wherein $R^1$ and m are as already defined above.

Suitable solvents for Step F can be selected from the group consisting of $C_3$–$C_{12}$ linear and branched alkanes, $C_1$–$C_6$ linear and branched halogenated alkanes, $C_5$–$C_7$ cycloalkanes, $C_6$–$C_{10}$ aromatic hydrocarbons, dialkyl ethers wherein each alkyl is independently a $C_1$–$C_6$ alkyl, $C_4$–$C_8$ dialkoxyalkanes, $C_4$–$C_6$ cyclic ethers and diethers, $C_6$–$C_8$ aromatic ethers, and $C_1$–$C_6$ alkyl alcohols. Exemplary solvents include carbon tetrachloride, chloroform, methylene chloride, 1,2-dichloroethane (DCE), 1,1,2-trichloroethane (TCE), 1,1,2,2-tetrachloroethane, cyclohexane, toluene, o- and m- and p-xylene, ethylbenzene, ethyl ether, MTBE, THF, dioxane, 1,2-dimethoxyethane (DME), anisole, phenetole, methanol, ethanol, n- and iso-propanol, and tert-butyl alcohol.

In one embodiment, the solvent is selected from the group consisting of $C_2$–$C_6$ linear and branched halogenated alkanes, dialkyl ethers wherein each alkyl is independently a $C_1$–$C_4$ alkyl, $C_4$–$C_6$ cyclic ethers and diethers, and $C_1$–$C_4$ alkyl alcohols. In an aspect of the preceding embodiment, the solvent is a $C_1$–$C_4$ alkyl alcohol. In another aspect of the preceding embodiment, the solvent is methanol.

The solvent can also be a mixture comprising water and an organic co-solvent. Suitable co-solvents include the organic solvents set forth in the preceding two paragraphs. In one embodiment, the co-solvent is a $C_1$–$C_6$ monohydric alcohol. In an aspect of this embodiment, the co-solvent is methanol or ethanol. The water can comprise from about 5 to about 95 volume percent based on the total volume of solvent. It has been found, however, that significant amounts of water (i.e., more than about 20 volume percent) can reduce the cis/trans selectivity of the hydrogenation. The use of 1:2 methanol/water solvent systems with HBr, for example, has been found to reduce selectivity dramatically compared to the use of methanol alone (e.g., 11:1 v. 23:1). Accordingly, in a preferred embodiment, the amount of water in the water-organic co-solvent mixture (e.g., water/methanol) is no more than about 20 vol%.

The hydrogenation of the oxime VI can be conducted over a wide range of temperatures, although the temperature is typically in the range of from about −25 to about 200° C. (e.g., from about −20 to about 100°). In one embodiment, the temperature is in the range of from about −10 to about 20° C. In another embodiment, the temperature is from about −5 to about 5° C.

The pressure is not a critical aspect in Step F, although atmospheric and superatmospheric pressures tend to be expedient. In one embodiment, the pressure is at least about 2 psig (115 kPa). In another embodiment, the pressure is in the range of from about 10 psia (68.9 kPa) to about 10,000 psia (68,950 kPa) (e.g., from about 50 psia (345 kPa) to about 1,000 psia (6,895 kPa)).

In one embodiment, the hydrogenation is conducted at a temperature in the range of from about −20 to about 100° C. and at a pressure of from about 2 psig (115 kPa) to about 1000 psig (6996 kPa). In another embodiment, the hydrogenation is conducted at a temperature in the range of from about −5 to about 20° C. and at a pressure in the range of from about 10 psig (167 kPa) to about 500 psig (3549 kPa). In still another embodiment, the hydrogenation is conducted at a temperature in the range of from about −10 to about 10° C. and at a pressure in the range of from about 10 psig (170 kPa) to about 100 psig (791 kPa).

The hydrogenation catalyst comprises palladium, which can be supported or unsupported. Suitable catalyst supports include carbon, silica, alumina, silicon carbide, aluminum fluoride, and calcium fluoride. Exemplary palladium catalysts include Pd black (i.e., fine metallic palladium particles) and Pd/C (i.e., palladium on a carbon support). Pd black is an effective catalyst, but results have been found to depend upon on the choice of vendor. Pd/C is a preferred catalyst.

The hydrogen source is typically hydrogen gas, optionally in admixture with a carrier gas that is inert to the process of the invention (e.g., nitrogen or a noble gas such as helium or argon).

The hydrogenation can be carried out in batches or continuously in various types of reactors such as a fixed bed reactor or an agitated slurry reactor in which the slurry of gas, solvent, oxime VI, HBr, and Pd catalyst is continuously agitated by mechanical or gas means. A suitable reaction vessel for relatively small scale, batch-wise hydrogenations is an autoclave equipped with a stirrer or rocker to agitate the reaction mixture. In a batch process, the order of addition of oxime VI, solvent, acid, and hydrogenation catalyst to the reaction vessel (also referred to herein as the reaction "pot") is not critical. The reactants and reagents can, for example, be added concurrently, either together or separately, or they can be added sequentially in any order. In one embodiment, oxime VI pre-mixed with the solvent is charged to the reaction vessel followed by addition of HBr, and then the Pd catalyst. The hydrogenation can then be conducted by charging hydrogen gas, optionally in admixture with one or more inert gases, to the vessel containing the mixture comprising oxime VI, solvent, HBr and Pd catalyst, and then agitating the mixture under reaction conditions.

Any amount of HBr, Pd catalyst and hydrogen can be employed which results in the formation of at least some of Compound VII. Of course, the maximum conversion of Compound VI and maximum yield of Compound VII is normally desired, and relative proportions of reactants and reagents suitable for this purpose are typically employed.

The HBr is suitably employed in Step F in an amount of at least about 0.5 equivalents per equivalent of Compound VI, and is typically employed in an amount of at least about 1 equivalent per equivalent of Compound VI. In one embodiment, the HBr is employed in an amount in the range of from about 0.5 to about 2 equivalents per equivalent of Compound VI. In another embodiment, the amount of HBr is in the range of from about 0.75 to about 1.25 equivalents per equivalent of VI. In still another embodiment, the amount of HBr is in the range of from about 0.95 to about 1.05 equivalents per equivalent of VI.

In one aspect of the process, the amount of HBr is in the range of from about 0.95 to about 1.05 equivalents per equivalent of VI, and the hydrogenation temperature is in the range of from about −5 to about 5° C. In another aspect of the process, the catalyst is Pd/C, the amount of HBr is in the range of from about 0.95 to about 1.05 equivalents per equivalent of VI, and the hydrogenation temperature is in the range of from about −5 to about 5° C.

When the level of HBr employed in the process is greater about 1.25 equivalents, hydrogenation should be begun promptly after the addition of the acid to avoid formation of solvolysis by-products such as, when using methanol solvent,

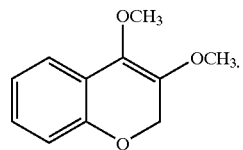

The uptake of hydrogen is not a critical process parameter, although at least a stoichiometric amount of hydrogen gas is typically employed.

Any amount of Pd catalyst can be employed which results in the formation of at least some of Compound VII. The amount of catalyst employed in step F is suitably at least about 0.01 mole percent Pd, and is typically in the range of from about 0.01 to about 5 (e.g., from about 0.1 to about 5) mole percent Pd, based on the total moles of Pd metal and Compound VII. In one embodiment, the amount of catalyst is in the range of from about 1 to about 5 (e.g., from about 2 to about 3) mole percent Pd metal.

The progress of any of the above-described reaction steps (i.e., Steps A, B, C, D, E and F) can be followed by monitoring the disappearance of a reactant (e.g., Compound VI or $H_2$ in Step F) and/or the appearance of the product using such analytical techniques as TLC, HPLC, NMR or GC.

The product resulting from the hydrogenation of oxime VI is typically in the form of an HBr salt, which can be treated with a base to provide free amine. Any organic or inorganic base which is capable of neutralizing the acidic hydrogenated mixture resulting from step F can be employed. Suitable bases include bases selected from the group consisting of alkali metal hydroxides, alkali metal carbonates, alkali metal oxides, $C_1$–$C_6$ alkoxides of alkali metals, alkaline earth metal hydroxides, alkaline earth metal oxides, tetra ($C_1$–$C_4$ alkyl)ammonium hydroxides, and tri-($C_1$–$C_4$ alkyl)amines. Exemplary bases include hydroxides, carbonates, and oxides of lithium, sodium and potassium; methoxides, ethoxides, and n- and iso-propoxides of lithium, sodium, and potassium; tetramethyl- and tetraethyl-ammonium hydroxide; triethylamine; and diisopropylethylamine. In one embodiment, the base is selected from the group consisting of alkali metal hydroxides. In an aspect of the preceding embodiment, the base is NaOH or KOH.

The base is typically employed in an amount sufficient to achieve complete neutralization of the Step F reaction product. The amount of base can suitably be at least about 1 equivalent per equivalent of Compound VII, and is typically in the range of from about 1 to about 5 equivalents per equivalent of Compound VII. In one embodiment, the amount of base is from about 1 to about 2 equivalents per equivalent of Compound VII. In another embodiment, the amount of base is in the range of from about 1 to about 1.5 equivalents per equivalent of Compound VII. The base can be charged to the reaction vessel containing the step F hydrogenated mixture, or the hydrogenated mixture can be charged to a vessel containing the base.

The base neutralization can be suitably conducted at a temperature in the range of from about –10 to about 110° C., and is typically conducted at a temperature in the range of from about 0 to about 80° C. In one embodiment, the temperature is in the range of from about 10 to about 30° C.

Alternatively, the base treatment of the Step F product can comprise eluting the hydrogenated mixture through a suitable ion exchange column, such as elution through Dowex® (available from Dow Chemical) or Amberlyst-IRA (available from Rohm & Haas).

Following the treatment with base, Compound VII in a free base form can be isolated from the reaction mixture by conventional means, such as by filtration to remove solids, solvent wash, concentration (e.g., by vacuum removal of solvent), and crystallization.

It is to be understood that, unless stated to the contrary, any references herein to Compounds I, II-A, II-B, II-C, III, VI, and VII also apply to Compounds I*, II-A*, II-B*, II-C*, III*, VI* and VII*.

The crude cis-aminochromanol product VII obtained from Step F is enantiomerically enriched in either the S,S-isomer or the R,R-isomer; i.e., the product has an significant enantiomeric excess (ee) of the S,S-isomer over the R,R-isomer or vice versa. Product VII may suitably be characterized as having an ee of at least about 60%, and typically has an ee of at least about 90%. The product can have an ee of 95% or more (e.g., 99%). To the extent that product VII is a mixture of optical isomers, the desired isomer (either S,S- or R,R) can be purified by forming diastereomeric salts of the isomers and separating the salts by fractional crystallization. In one embodiment, the isomer of Compound VII can be purified by:

(1) forming a solution comprising Compound VII, a chiral acid, and solvent;

(2) crystallizing from the solution a salt which contains predominantly either the S,S- or R,R-isomer; and (3) if the precipitated salt crystals consist predominantly of the desired isomer, separating the salt crystals from the mother liquor; and (4) if the mother liquor consists predominantly of the desired isomer, separating the salt crystals from the mother liquor and recovering the isomer from the mother liquor.

In an aspect of the preceding embodiment, the S,S-isomer (i.e., Compound VII*) can be purified by:

(1) forming a solution comprising Compound VII*, a chiral acid, and solvent;

(2) crystallizing from the solution a salt which contains predominantly either the S,S- or R,R-isomer; and (3) if the precipitated salt crystals consist predominantly of the S,S-isomer, separating the salt crystals from the mother liquor; and (4) if the mother liquor consists predominantly of the S,S-isomer, separating the salt crystals from the mother liquor and recovering the S,S-isomer from the mother liquor.

Suitable chiral acids include optically active forms of tartaric acid, mandelic acid, camphoric acid, 10-camphorsulfonic acid, pyroglutamic acid, O,O-diacetyltartaric acid, O,O-dibenzoyltartaric acid, O,O-di-4-toluyltartaric acid, and N-acetyl derivatives of amino acids such as N-acetylleucine. A preferred chiral acid is (S)-mandelic acid or (R)-mandelic acid. The chiral acid is especially (S)-mandelic acid, and the crystallized (S)-mandelate salt resulting from crystallizing step (2) is a salt of the S,S-isomer.

The solvent can be any organic or inorganic substance, or combinations thereof, which can dissolve Compound VII and the chiral acid and is chemically inert thereto. Suitable solvents include water, $C_1$–$C_6$ monohydric alcohols (e.g., methanol, ethanol, n-propanol, n-butanol, n-pentanol, isopropanol, and sec-butyl alcohol), $C_2$–$C_8$ polyhydric alcohols (e.g., ethylene glycol, propylene glycol, and glycerol), $C_1$–$C_4$ nitrites (e.g., acetonitrile and propionitrile), N,N-di-$C_1$–$C_6$ alkyl tertiary amides of $C_1$–$C_6$ alkylcarboxylic acids (e.g., DMF), aliphatic $C_2$–$C_6$ ethers and di-ethers (e.g., ethyl ether, MTBE and dimethoxyethane), and $C_4$–$C_6$ cyclic ethers and di-ethers (e.g., THF and dioxane). In one embodiment, the solvent is selected from the group consisting of $C_1$–$C_6$ monohydric alcohols, aliphatic $C_2$–$C_6$ ethers and di-ethers and $C_4$–$C_6$ cyclic ethers and di-ethers. In an aspect of the preceding embodiment, the solvent is an alcohol such as methanol or ethanol.

In another embodiment, the solvent is a mixture comprising water and an organic co-solvent. In an aspect of this embodiment, water comprises at least about 5 volume percent of the solvent (e.g., from about 5 to about 95 volume percent) based on the total volume of solvent. In another aspect of this embodiment, the aqueous solvent comprises from about 30 to about 70 volume percent (e.g., from about 40 to about 60 volume percent) water, with the balance of the solvent being organic co-solvent. Suitable co-solvents include the organic solvents set forth in the preceding paragraph. In one embodiment, the co-solvent is a $C_1$–$C_6$ monohydric alcohol. In an aspect of this embodiment, the co-solvent is methanol or ethanol.

The crystallization of the S,S- or R,R-isomer as set forth in step (2) above can be accomplished using conventional techniques, such as by cooling the solution or by concentrating the solution via vacuum or evaporative removal of solvent. If the resulting crystals are predominantly the S,S-isomer, the crystals can then be separated by filtration and followed optionally by the washing and drying of the filter cake. If the precipiated crystals are predominantly the R,R-isomer, a salt which contains predominantly the S,S isomer can be obtained from the mother liquor, such as by evaporative or vacuum removal of the solvent.

The crystallized salt of the recovered isomer (e.g., the S,S-isomer) can then be broken by treating the salt with base. In a typical procedure, the crystallized salt can be slurried in an organic solvent, the slurry mixed with aqueous base resulting in a biphasic mixture, and the organic layer containing the isomer separated from the aqueous layer. The formation of the slurry and the biphasic mixture is suitably conducted at temperatures in the range of from about 0 to about 100° C., and is typically conducted at a temperature of from about 10 to about 60° C. In one embodiment, the temperature is in the range of from about 15 to about 35° C. The base can be any of the bases set forth above in the description of treating the HBr salt of aminochromanol VII. The base can also be an alkanolamine (e.g., ethanolamine), a hydroxylamine (e.g., hydroxylamine per se, N-methylhydroxylamine, N,N-dimethylhydroxylamine, or N-ethylhydroxylamine), or a diamine (e.g., ethylenediamine, tetramethylenediamine, or hexamethylenediamine). The organic solvent can suitably be selected from $C_1$–$C_{12}$ linear and branched alkanes, $C_1$–$C_{12}$ linear and branched halogenated alkanes, $C_5$–$C_{10}$ cycloalkanes, $C_6$–$C_{14}$ aromatic hydrocarbons, dialkyl ethers wherein each alkyl is independently a $C_1$–$C_{10}$ alkyl, $C_4$–$C_8$ dialkoxyalkanes, $C_4$–$C_8$ cyclic ethers and diethers, $C_6$–$C_8$ aromatic ethers, $C_2$–$C_{10}$ dialkyl ketones wherein each alkyl is independently $C_1$–$C_8$ alkyl, $C_1$–$C_6$ alkyl esters of $C_1$–$C_6$ alkylcarboxylic acids, primary $C_1$–$C_{10}$ alkyl alcohols, secondary $C_3$–$C_{10}$ alkyl alcohols, tertiary $C_4$–$C_{10}$ alkyl alcohols, primary amides of $C_1$–$C_6$ alkylcarboxylic acids, N—$C_1$–$C_6$ alkyl secondary amides or N,N-di-$C_1$–$C_6$ alkyl tertiary amides of $C_1$–$C_6$ alkylcarboxylic acids, $C_2$–$C_6$ aliphatic nitriles, and $C_7$–$C_{10}$ aromatic nitriles. Exemplary solvents include carbon tetrachloride, chloroform, methylene chloride, 1,2-dichloroethane (DCE), 1,1,2-trichloroethane (TCE), 1,1,2,2-tetrachloroethane, cyclohexane, toluene, o- and m- and p-xylene, ethylbenzene, ethyl ether, MTBE, THF, dioxane, 1,2-dimethoxyethane (DME), anisole, phenetole, acetone, methyl ethyl ketone (MEK), methyl acetate, ethyl acetate, IPAc, ethanol, n- and iso-propanol, tert-butyl alcohol, dimethylformamide (DMF), acetonitrile, propionitrile, benzonitrile, and p-tolunitrile.

In an aspect of the process of purifying the S,S-optical isomer VII*, a solution of cis-aminochromanol and (S)-mandelic acid is formed, the (S)-mandelate salt of the S,S-isomer is crystallized and separated from the mother liquor, and the crystallized salt is broken by treatment with ethanolamine to afford the purified S,S-aminochromanol isomer.

Another embodiment of the process of the invention is a process for preparing hydroxychromanone 6:

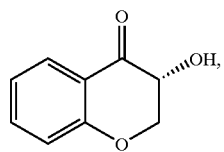

which comprises:

(C) adding acid chloride 4a:

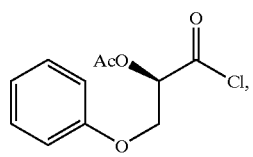

to a solution of $AlCl_3$ in a halogenated hydrocarbon solvent at a temperature of less than about 0° C. to form acetoxy chromanone 5:

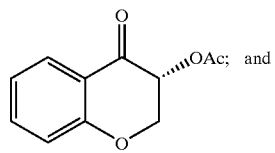

(D) reacting Compound 5 at a temperature of less than about 0° C. with lithium peroxide or lithium hydroperoxide in an ethereal or alcoholic solvent to form Compound 6.

Aspects of the preceding embodiment include the process as just set forth, wherein:

(i) the temperature in Step C is in a range of from about −20 to about 0° C.;

(ii) the halogenated hydrocarbon solvent in Step C is a $C_1$–$C_6$ linear or branched halogenated alkane (e.g., methylene chloride);

(iii) $AlCl_3$ is employed in Step C in an amount of from about 0.1 to about 5 equivalents per equivalent of Compound 4a;

(iv) the temperature in Step D is in a range of from about −20 to about 0° C.;

(v) the solvent in Step D is selected from the group consisting of dialkyl ethers wherein each alkyl is independently a $C_1$–$C_4$ alkyl, $C_4$–$C_6$ cyclic ethers and diethers, and $C_1$–$C_4$ alkyl alcohols;

(vi) the lithium peroxide or hydroperoxide (e.g., LiOOH) is employed in Step D in an amount of from about 1 to about 5 equivalents per equivalent of Compound 5; and (vii) the process incorporates one or more of any of aspects (i) to (vi).

In another embodiment of the process of the invention is a process for preparing oxime 7 which comprises Steps C and D as just set forth above and further comprises:

(E) treating Compound 6 with hydroxylamine or an acid salt thereof to form oxime 7:

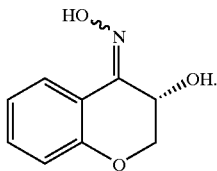

Aspects of the preceding embodiment include the process as set forth, wherein:
(i) Compound 6 is treated with hydroxylamine sulfate;
(ii) the temperature is in a range of from about 15 to about 30° C.;
(iii) hydroxylamine is employed in an amount of at least about 2 equivalents per equivalent of 6;
(iv) the treating is conducted in a two-phase solvent consisting of an aqueous ether, optionally in the presence of a buffer (e.g., NaOAc); and
(v) the process incorporates one or more of any of aspects (i) to (iv).

In still another embodiment of the process of the invention is a process for preparing aminochromanol 8 which comprises Steps C, D, and E as just set forth above and further comprises:
(F) hydrogenating in the presence of a palladium catalyst a mixture comprising Compound 7, an ethereal or alcoholic solvent, and HBr to form aminochromanol 8:

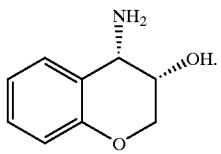

Aspects of the preceding embodiment include the process as set forth, wherein:
(i) the catalyst in Step F is Pd/C;
(ii) the amount of HBr is in the range of from about 0.95 to about 1.05 equivalents per equivalent of 7;
(iii) the hydrogenation is conducted at a temperature in the range of from about −5 to about 5° C.;
(iv) the hydrogenation is conducted at a temperature in the range of from about −20 to about 100° C. and at a pressure of at least about 2 psig (115 kPa);
(v) the process incorporates the combination of (i) and (ii);
(vi) the process incorporates the combination of (i) and (iii);
(vii) the process includes the combination of (i), (ii), and (iii); and
(viii) the process includes the combination of (i), (ii) and (iv).

As used herein, the term "$C_1$–$C_6$ alkyl" (which may alternatively be referred to herein as "$C_{1-6}$ alkyl") means linear or branched chain alkyl groups having from 1 to 6 carbon atoms and includes all of the hexyl alkyl and pentyl alkyl isomers as well as n-, iso-, sec- and t-butyl, n- and isopropyl, ethyl and methyl. "$C_1$–$C_4$ alkyl" means n-, iso-, sec- and t-butyl, n- and isopropyl, ethyl and methyl. Similar terms (e.g., "$C_1$–$C_3$ alkyl") have analogous definitions.

The term "$C_1$–$C_6$ alkoxy" means an —O-alkyl group wherein alkyl is $C_1$ to $C_6$ alkyl as defined above. "$C_1$–$C_4$ alkoxy" has an analogous meaning; i.e., it is an alkoxy group selected from methoxy, ethoxy, n-propoxy, isopropoxy, n-butoxy, isobutoxy, tert-butoxy, and sec-butoxy. Similar terms (e.g., "$C_1$–$C_3$ alkoxy") have analogous definitions.

The term "halogen" (which may alternatively be referred to as "halo") refers to fluorine, chlorine, bromine and iodine (alternatively, fluoro, chloro, bromo, and iodo).

The term "halogenated $C_1$–$C_6$ alkyl" (which may alternatively be referred to as "$C_1$–$C_6$ haloalkyl" or "$C_{1-6}$ haloalkyl") means a $C_1$ to $C_6$ linear or branched alkyl group as defined above with one or more halogen substituents. The terms "halogenated $C_1$–$C_4$ alkyl" and "halogenated $C_1$–$C_3$ alkyl" have analogous meanings. The term "fluorinated $C_1$–$C_6$ alkyl" (or "$C_1$–$C_6$ fluoroalkyl" or "$C_{1-6}$ fluoroalkyl") means a $C_1$ to $C_6$ linear or branched alkyl group as defined above with one or more fluorine substituents. The terms "fluorinated $C_1$–$C_4$ alkyl" and "fluorinated $C_1$–$C_3$ alkyl" have analogous meanings. Representative examples of suitable fluoroalkyls include the series $(CH_2)_{0-3}CF_3$ and $(CH_2)_{0-2}CF_3$ (i.e., trifluoromethyl, 2,2,2-trifluoroethyl, and 3,3,3-trifluoro-n-propyl), 1-fluoroethyl, 2-fluoroethyl, 2,2-difluoroethyl, 3,3,3-trifluoroisopropyl, 1,1,1,3,3,3-hexafluoroisopropyl, and perfluorohexyl.

The term "halogenated $C_1$–$C_6$ alkoxy" (which may alternatively be referred to as "$C_1$–$C_6$ haloalkoxy" or "$C_{1-6}$ haloalkoxy") means a $C_1$ to $C_6$ linear or branched alkyl group as defined above with one or more halogen substituents. The terms "halogenated $C_1$–$C_4$ alkoxy" and "halogenated $C_1$–$C_3$ alkoxy" have analogous meanings. The term "fluorinated $C_1$–$C_6$ alkoxy" (which may alternatively be referred to as "$C_1$–$C_6$ fluoroalkoxy") means a $C_1$–$C_6$ alkoxy group as defined above wherein the alkyl moiety has one or more fluorine substituents. The terms "fluorinated $C_1$–$C_4$ alkoxy" and "fluorinated $C_1$–$C_3$ alkoxy" have analogous meanings. Representative examples include the series $O(CH_2)_{0-3}CF_3$ (i.e., trifluoromethoxy, 2,2,2-trifluoroethoxy, 3,3,3-trifluoro-n-propoxy, etc.), 1,1,1,3,3,3-hexafluoroisopropoxy, and so forth.

The term "$C_3$–$C_8$ cycloalkyl" refers to a cyclic ring selected from cyclopropyl, cyclobutyl, cyclopentyl, cyclohexyl, cycloheptyl, and cyclooctyl. "$C_3$–$C_6$ cycloalkyl" has an analogous meaning.

The term "alkali metal" refers to a metal of Group Ia of the Periodic Table, including but not limited to lithium, sodium, and potassium.

Abbreviations used in the instant specification include the following:
Ac=acetic or acetate
AcCl=acetyl chloride
AIDS=acquired immune deficiency syndrome
ARC=AIDS related complex
DCE=1,2-dichloroethane
DME=1,2-dimethoxyethane
DMF=dimethylformamide
DSC=differential scanning calorimetry
EtOH=ethanol
IPAc=isopropyl acetate
KF=Karl Fisher titration for water
Me=methyl
MeCN=acetonitrile
MeOH=methanol
MTBE=methyl tert-butyl ether NMP=N-methylpyrrolidone
psia=pounds per square inch (absolute)
psig=pounds per square inch (gauge)
THF=tetrahydrofuran
TCE=1,1,2-trichloroethane
XRPD=X-ray powder diffraction The following examples serve only to illustrate the invention and its practice. The examples are not to be construed as limitations on the scope or spirit of the invention.

EXAMPLE 1

Preparation of 3(R)-Hydroxychroman-4-one

Step A: Preparation of methyl glycidate

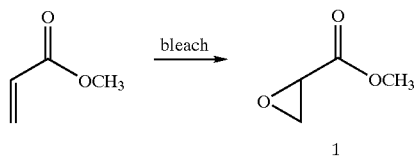

In a 5 L round bottom flask fitted with an overhead stirrer was charged 5.25% aq. NaOCl (3.79 L, 2.67 mol). The yellow-green solution was then cooled to 10° C., then methyl acrylate (215 mL, 1.89 mol) was added. The resulting cloudy solution was stirred for two hours while slowly warming to room temperature, where it became colourless, then extracted with three 500 mL portions of CH$_2$Cl$_2$. The combined organic extracts were dried (MgSO$_4$), filtered and concentrated. The residues were then carefully distilled through a short-path apparatus (b.p. 45° C., 1 torr), affording 116.07 g of methyl glycidate 1 as a clear oil.

Step B: Phenol kinetic resolution and ester hydrolysis

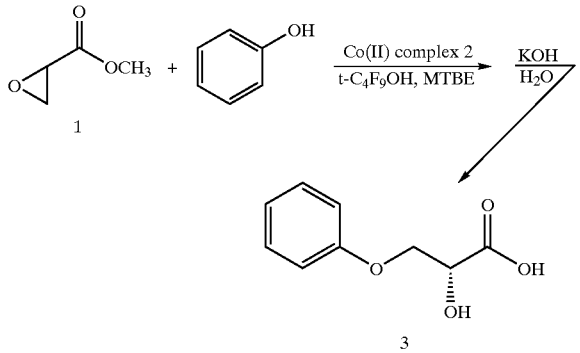

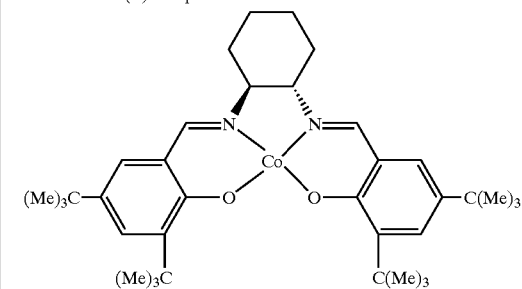

To a solution of (R,R)-salen cobalt (II) complex 2 (5.91 g, 0.00980 mol) in CH$_2$Cl$_2$ (100 mL) cooled to 0° C. was added perfluoro-t-butanol (2.74 mL, 0.0196 mol). The resulting solution was warmed to room temperature while stirring, held at room temperature for two hours while stirring, and then concentrated in vacuo. 3 Å molecular sieves (10.00 g) were added, followed by methyl glycidate (50.00 g, 0.4897 mol). The resulting mixture was cooled to −10° C., and phenol (20.95 g, 0.2226 mol) was added, followed by a second portion of perfluoro-t-butanol (1.37 mL, 0.00981 mol) and MTBE (14 mL). The reaction was stirred for 3 days at −10° C., with conversion assayed by LC (Zorbax, Rx-C8, 30% MeCN, 70% 0. 1% aq. H$_3$PO$_4$, r.t. (phenol) 8.85 min, (product) 6.74 min.). The molecular sieves along with some red solids were filtered off on a pad of Celite, washing extensively with CH$_2$Cl$_2$. The filtrate was concentrated. 20 mL of water was added to the material and the red-brown mixture was cooled to 0° C. 22.5% aq. KOH (100 mL) was slowly added, keeping the temperature below 10° C. The mixture was immediately filtered, washed with water, and the filtrate was extracted with two 150 mL portions of CH$_2$Cl$_2$. The aqueous phase was transferred to a 500 mL 3-neck round-bottom flask fitted with an overhead stirrer, cooled to 0° C., and 75 mL of conc. HCl were slowly added. The resulting precipitate was collected on a medium frit, and the cake was washed with 20 mL 1 M HCl, then dried with a N$_2$ sweep for 16 h to afford 43.77 g (~100%) of α-hydroxyacid 3. The material isolated was contaminated with a crystalline, water-soluble material, most like KCl from the isolation. $^{13}$C NMR (CD$_3$OD): δ173.8, 158.7, 129.1, 120.8, 114.4, 69.7 (2C).

The ee was assayed by reforming the methyl ester as follows:

To a solution of conc. H$_2$SO$_4$ (50 μL) in MeOH (5 mL) at 0° C. was added 3 (201.7 mg, 1.12 mmol). The resulting mixture was stirred for 1 h at room temperature, then diluted with 5 mL CH$_2$Cl$_2$ and 5 mL water. The layers were separated, and the organic layer dried (MgSO$_4$), filtered, and concentrated. The residues were analyzed by chiral HPLC (Chiralcel OD, 20% EtOH in hexanes, r.t. (minor) 6.61 min., (major) 11.28 min.) at 92.8%ee.

Step C: Acetate formation

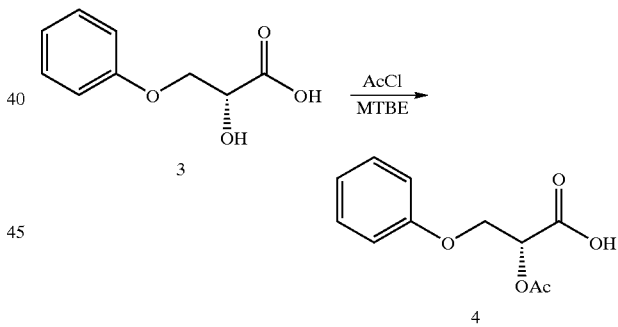

Hydroxyacid 3 (42.32 g, 0.232 mol) was suspended in MTBE (460 mL) under N$_2$ in a 1 L three-neck round-bottom flask fitted with a reflux condenser and overhead stirrer. Acetyl chloride (66 mL, 0.928 mol) was added, and the resulting mixture was heated to reflux. After 1.5 hrs, an additional portion was of acetyl chloride was added (16.5 mL, 0.232 mol), and likewise at 2.5 hrs, and 4 hrs. The mixture was refluxed for 1 hour after the last addition, where it had reached 99% conversion (Zorbax, Rx-C8, 50% MeCN, 50% 0.1% aq. H$_3$PO$_4$, r.t. (s.m.) 3.13 min, (product) 4.25 min.). The reaction was cooled to room temperature and concentrated in vacuo. The residues were dissolved in CH$_2$Cl$_2$ (100 mL) and concentrated again to remove residual acetyl chloride. Some water-soluble solids were present throughout the procedure, and were likely KCl remaining from the isolation of 3. $^1$H NMR (CDCl$_3$): δ7.31 (m, 2H), 7.01 (m, 1H), 6.95 (m, 1H), 5.51 (dd, J=5.3, 2.9 Hz, 1H), 4.45 (dd, J=10.6, 5.3 Hz, 1H), 4.38 (dd, J=10.6, 2.9 Hz, 1H), 2.22 (s, 3H).

Step D: Intramolecular Friedel-Crafts Acylation

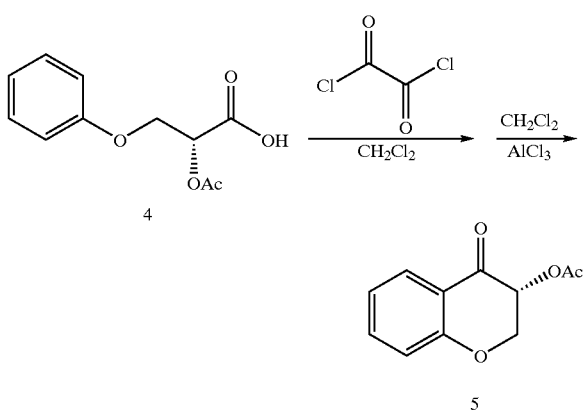

To a solution of acetoxyacid 4 (0.232 mol) in CH$_2$Cl$_2$ (230 mL) at 15° C. was added oxalyl chloride (26 mL, 0.298 mol), then DMF (0.90 mL, 0.012 mol). Vigorous bubbling was observed. The resulting solution was stirred for 1 h at room temperature ($^1$H NMR showed complete conversion), then concentrated. To a 2 L, three-neck round-bottom flask fitted with a 500 mL addition funnel and overhead stirrer, purged with N$_2$, was charged AlCl$_3$ (62.25 g, 0.467 mol) and CH$_2$Cl$_2$ (460 mL). The mixture was cooled to -13° C. and the addition funnel was charged with a solution of the acid chloride in 230 mL CH$_2$Cl$_2$. The acid chloride solution was slowly added portionwise (solids and all) such that the temperature of the reaction didn't exceed -9° C. The resulting black mixture was stirred 40 min. at -13° C., at which point LC indicated complete conversion (Zorbax, Rx-C8, 50% MeCN, 50% 0.1% aq. H$_3$PO$_4$, r.t. (s.m.) 4.25 min, (product) 5.76 min). The reaction was quenched by slow addition of 700 mL 1 M HCl (temperature never exceeded +13° C.). The layers were separated, and the aqueous phase extracted with CH$_2$Cl$_2$ (250 mL). The combined organic layers were washed with half saturated aqueous NaHCO$_3$ (500 mL), then brine (500 mL), dried, filtered and concentrated to afford 45.03 g (94%, crude) of a brown oil that crystallized upon standing. The enantiomeric excess of the product 5 was deterrmined to be 92.8% ((R,R)-Whelk-O1, 1% EtOH in hexanes, r.t. (minor): 13.81 min., r.t. (major): 15.12 min.). $^1$H NMR (CDCl$_3$): δ7.91 (dd, J=8.0, 1.5 Hz, 1H), 7.52 (m, 1H), 7.07 (m, 1H), 7.01 (d, J=8.5 Hz, 1H), 5.67 (apparent q, J=5.5 Hz, 1H), 4.58 (dd, J=11.1, 5.5 Hz, 1H), 4.42 (apparent t, J=11.3 Hz, 1H). $^{13}$C NMR (CDCl$_3$): δ188.0, 169.5, 161.3, 136.5, 127.6, 122.1, 119.6, 117.8, 69.4, 68.3, 20.6.

Step E: Acetate cleavage

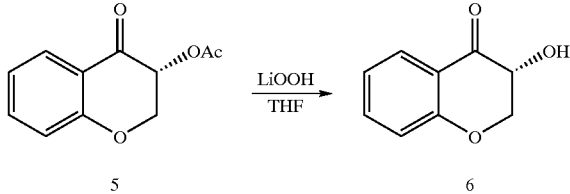

In a 2 L 3-neck round-bottom flask fitted with an overhead stirrer and a 250 mL addition funnel under N$_2$ was suspended LiOH.H$_2$O (27.49 g, 0.655 mol) in THF (510 mL). Hydrogen peroxide (30% aq., 121 mL, 1.55 mol) was added, and the solids immediately became fluffy. The resulting mixture was stirred for 25 min. at room temperature, then cooled to -13° C. and a solution of 5 in 130 mL THF was addded dropwise. The resulting mixture was stirred for 30 min. at -15° C. at which point LC showed complete conversion (Zorbax, Rx-C8, 50% MeCN, 50% 0.1% aq. H$_3$PO$_4$, r.t. (s.m.) 5.76 min, (product) 3.62 min.) The reaction was quenched slowly with 1.25 L of 10% aq. NaHSO$_3$, keeping the temperature below 20° C. MTBE (500 mL) was added, and the layers were separated. The aqueous phase was extracted with 500 mL MTBE, and the combined organic phases were washed with brine, dried (MgSO$_4$), filtered and concentrated to afford 6 (31.52 g, 88%) as an off-white solid in 91.9%ee (GC of trifluoroacetate, Chiraldex G-TA, 20 m×0.32 mm, 110° C., isothermal, r.t. (major) 15.65 min., r.t. (minor) 16.10 min.). $^1$H NMR (CDCl$_3$): δ7.84 (dd, J=7.8, 1.7 Hz, 1H), 7.48 (m, 1H), 7.02 (m, 1H), 6.95 (d, J=8.4 Hz), 4.61 (m, 2H), 4.13 (m, 1H), 3.95 (br s, 1H). $^{13}$C NMR (CDCl$_3$): δ194.4, 162.1, 136.6, 127.3, 121.8, 118.8, 117.9, 70.5, 69.1.

EXAMPLE 2

Preparation of 3(R)-Hydroxychroman-4-one Oxime

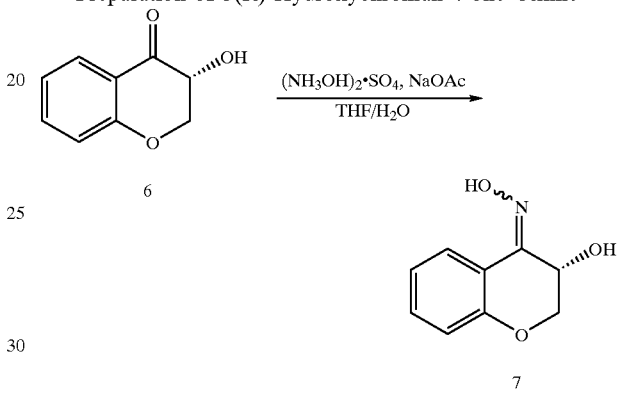

To a solution of 6 (from Example 1, 1.69 g, 10.3 mmol) in THF (20 mL) was added hydroxylamine sulfate (3.37 g, 20.5 mmol), sodium acetate trihydrate (5.58 g, 41.0 mol), and water(5 mL). The resulting two-phase mixture was stirred for 20 h at room temperature, at which point conversion was complete (Zorbax, Rx-C8, 30% MeCN, 70% 0.1% aq. H$_3$PO$_4$, r.t. (s.m.) 5.99 min, (product) 4.78 min.). MTBE (25 mL) and water (25 mL) were added. The layers were separated, and the organic phase washed with brine (25 mL), dried (MgSO$_4$), filtered and concentrated to give crude 7.

EXAMPLE 3

Preparation of cis-Aminochromanol

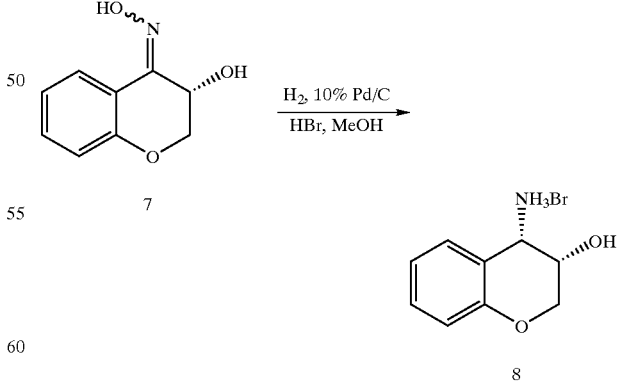

To a solution of 7 (1.52 g, 8.50 mmol) in methanol (30 mL) at 0° C. was added 48% aqueous HBr (0.961 ml, 8.50 mmol) and 1.15 g of palladium on carbon (Johnson Mathey, RM95598). The mixture was hydrogenated at 40 psig for 24 hours. The solution was filtered through a pad of celite which was washed with several portions of methanol. The filtrate was concentrated to afford (S,S)-8 as a pale yellow solid (1.92 g, 94%). Chiral HPLC analysis of the mixture showed the enantiomeric excess of 8 to be 92% and the cis trans ratio to be 24:1. $^1$H NMR (CD$_3$OD): δ7.43 (dd, J=7.9, 1.3 Hz, 1H), 7.30 (m, 1H), 7.02 (m, 1H), 6.89 (dd, J=8.3, 1.1 Hz, 1H), 4.62 (d, J=4.9 Hz, 1H), 4.35 (m, 1H), 4.22 (ddd, J=11.6, 3.4, 1.0 Hz, 1H), 4.07 (dd, J=11.6, 8.2 Hz). $^{13}$C NMR (CD$_3$OD): δ154.3, 130.4, 129.3, 121.1, 116.9, 116.3, 65.4, 61.7, 48.8.

EXAMPLE 4

Preparation of cis-Aminochromanol

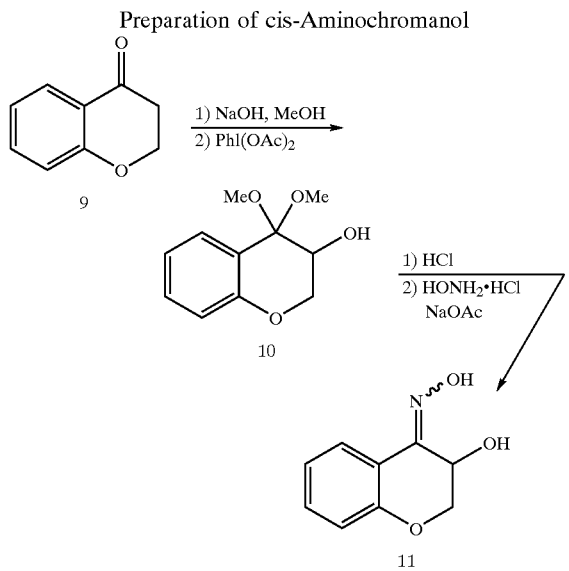

To a solution of NaOH (1.6 Kg, 39 mol, 3.0 equiv. assuming 97% purity) in MeOH (11.1 L) at −10° C. was added a solution of chromanone (9, 2.0 Kg, 13 mol, 1.0 equiv. assuming 99% purity) in MeOH (8.2 L) precooled to −10° C. The resulting yellow solution was aged 5 minutes at −10° C. and a slurry of iodobenzene diacetate (4.44 Kg, 13 mol, 1.00 equiv assuming 97% purity) in MeOH (12.2 L) was added at −10° C. The dark orange reaction mixture was aged 0.5 hour at −10° C. and was warmed to 20° C. over 1 hour. The reaction mixture was aged at 20° C. for 3 hours and was transferred to a solution of 4N aqueous HCl (11.8 L, 45.5 mol, 3.5 equiv.) at 0–20° C. over >10 minutes. The yellow slurry was aged at 20–30° C. for 20 minutes and sodium acetate (2.74 kg, 33.4 mol, 2.5 equiv.) and hydroxylamine hydrochloride (1.86 kg, 26.7 mol, 2.0 equiv) were subsequently added in one portion. The reaction mixture was warmed up to 50° C., aged 1 hour and cooled back to room temperature. The solution was concentrated to a total volume of 28 L, was diluted with water (16 L) and was extracted with heptane (2×16 L). The methanolic aqueous layer was extracted with IPAc (2×16 L). The combined IPAc layers were washed with water (1×16 L), were concentrated and flushed with additional IPAc to a final volume of 5.6 L (KF<400 μg/ml). Heptane (1.9 L) was added over 30 minutes at 20° C., followed by more heptane (18.9 L) added over 30 minutes. The hydroxychromanone oxime 11 crystallized as a yellow solid. The mixture was cooled to −10° C., aged 2 hours, filtered and washed with 3 L of 3.7:1 heptane/IPAc at −10° C. and 3 L of heptane at 20° C. The oxime was dried under vacuum at 20° C. to give a light yellow solid (1.82 Kg, 75%). $^1$H NMR (400 MHz DMSO-d$_6$) Major isomer: δ9.70–9.93 (br, 1H), 8.35 (dd, 1H, J$_1$=7.8, J$_2$=1.6), 7.86 (dt, 1H, J$_1$=7.8, J$_2$=1.7), 7.54 (dt, 1H, J$_1$=11.7, J$_2$=1.1), 7.49 (dd, 1H, J$_1$=8.2 J$_2$=1.1), 5.68 (t, 1H, J$_1$=2.2), 4.91 (dd, 1H, J$_1$=12.4, J$_2$=2.3), 4.59 (dd, 1H, J$_1$=12.4, J$_2$=2.1), 4.13–4.38 (br, 1H). Selected minor isomer peaks: δ9.13 (dd, 1H, J$_1$=8.1, J$_2$=1.7), 7.91 (dt, 1H, J$_1$=7.9, J$_2$=1.7), 4.94 (dd, 1H, J$_1$=9.8, J$_2$=2.6), 4.76 (dd, 1H, J$_1$=12.8, J$_2$=2.8)

Step A: Hydrogenation and Treatment with Base

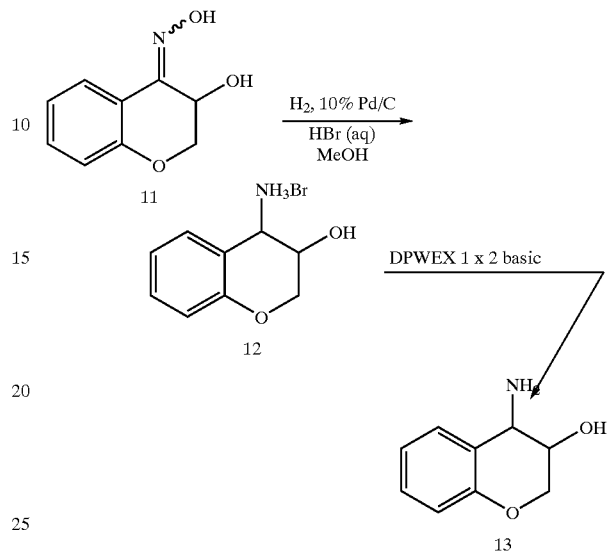

To a solution of oxime (11 2.51 Kg, 14.02 mol) in methanol (49 L) at 0° C. was charged 48% aqueous HBr (1.94 L) maintaining the temperature below 5° C. 10% Palladium on carbon (2 Kg, 62% water wet) was charged and the mixture was hydrogenated in a five-gallon, stirred autoclave at 5° C., 40 psig for 12 hr (cis/trans 20:1, 89% assay yield of cis isomer). The mixture was filtered through solka floc and washed with methanol to give a solution of the HBr salt 12 in methanol (85 L). The batch was eluted through Dowex 1×2 (19 L) on the base-cycle using methanol (72 L). The solution of free-base amine 13 was solvent switched to ethanol (44 L, KF≦550 ug/mL) under reduced pressure.

Step B: Mandelate Formation

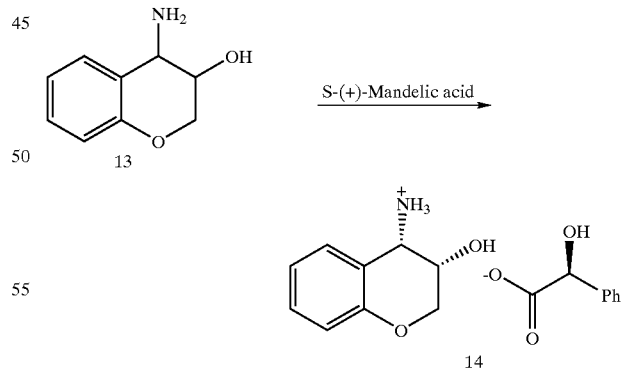

The free base amine 11 in ethanol was heated to 70° C. and S-mandelic acid (2.1 Kg, 14 mol) in ethanol (3 L) was added. The mixture was cooled to 15° C. over 3 hr. The salt 14 was isolated by filtration and washed with ethanol (3.5 L). The batch was dried under vacuum at 20° C. to give 1.688 Kg of dry cake (>96% ee, 38% overall yield).

Step C: Salt Break

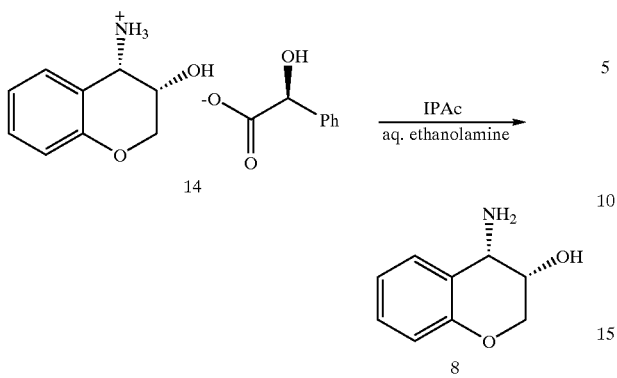

To a slurry of the mandelate salt (14, 1.688 Kg, mol) in isopropylacetate (16 L) at 15–20° C. was added 10% v/v aqueous ethanolamine (6.6 L). The resulting bi-phasic mixture was agitated for 30 minutes and settled for 20 minutes. The phases were cut and the aqueous layer was extracted with IPAc (3×8 L). The IPAc extracts were batch concentrated to 8 L at 40–50° C. (KF≦500 ug/mL). The batch was heated to 65–70° C. and n-heptane (8 L) was added over 30 minutes. The batch was cooled to 0–5° C. over 3 hr and the aminochromanol was isolated by filtration. The wet cake was washed with 1:1 IPAc/n-heptane at 0–5° C. (1.5 L) and dried under vacuum at 20° C. to give S,S-aminochromanol 8 as a colorless solid (0.75 Kg, 90%).

A differential scanning calorimetry curve was obtained for Compound 7 under a nitrogen atmosphere in a closed cup at a heating rate of 10° C./min using a DSC Model 2910 (DuPont Instruments). The curve showed an endotherm, due to melting, with an extrapolated onset temperature of about 110° C., a peak temperature of about 111° C. and an associated heat of about 193 Joules/gram. An X-ray powder diffraction pattern was also obtained for Compound 8 using a Philips Diffractometer APD 3720 with copper K alpha radiation. The following d-spacings were observed: 7.77, 7.54, 4.74, 4.62, 4.49, 4.47, 4.39, 3.98, 3.90, 3.78, 3.64, 3.30, 3.04, 2.70, 2.66, 2.61, 2.58, 2.53, and 2.43 angstroms. The specific rotation (1% solution in MeOH, 405 nm) was +177.9.

While the foregoing specification teaches the principles of the present invention, with examples provided for the purpose of illustration, the practice of the invention encompasses all of the usual variations, adaptations and/or modifications that come within the scope of the following claims.

What is claimed is:

1. A process for preparing a hydroxychromanone of Formula (I):

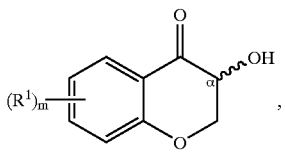

(I)

which comprises:

(C) adding an acid halide of Formula (II-C):

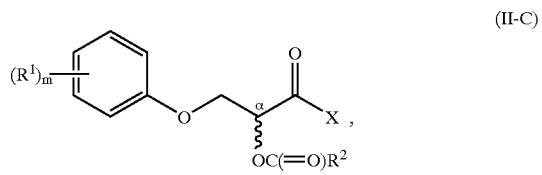

(II-C)

to a solution of AlCl$_3$ in a first organic solvent at a temperature of less than about 0° C. to form an alkylcarbonyloxy chromanone of Formula (III):

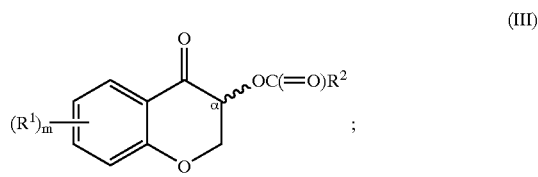

(III)

and (D) re actin g Compound III with an alkali metal per oxide or hydroperoxide in a second organic solvent at a temperature of less than about 0° C. to form Compound I;

wherein:

stereocenter α is in the R configuration or the S configuration;

each $R^1$ is independently halo, $C_1$–$C_6$ alkyl, halogenated $C_1$–$C_6$ alkyl, $C_1$–$C_6$ alkoxy, halogenated $C_1$–$C_6$ alkoxy, —CO$_2$$R^a$, —COR$^a$, —NR$^a$R$^b$, —NR$^a$—COR$^b$, —NR$^a$—CO$_2$R$^b$, —CO—NR$^a$R$^b$, —OCO—NR$^a$R$^b$, —NR$^a$CO—NR$^a$R$^b$, —S(O)$_p$—R$^a$, wherein p is an integer from 0 to 2, —S(O)$_2$—NR$^a$R$^b$, —NR$^a$S(O)$_2$—R$^b$, or —NR$^a$S(O)$_2$—NR$^a$R$^b$;

$R^2$ is $C_1$–$C_6$ alkyl;

X is halo;

each $R^a$ and $R^b$ is independently hydrogen, $C_1$–$C_4$ alkyl, or (CH$_2$)$_{0-3}$CF$_3$; and m is an integer from 0 to 4.

2. The process according to claim 1, which is a process for preparing a hydroxychromanone of Formula (I*):

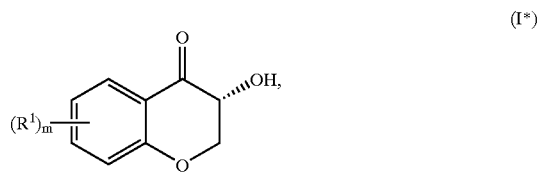

(I*)

which comprises:

(C) adding an acid halide of Formula (II-C*):

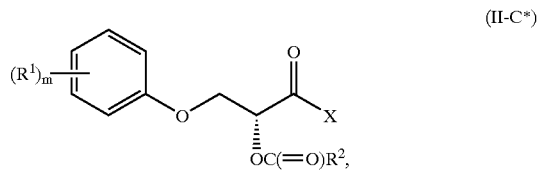

(II-C*)

to a solution of AlCl$_3$ in a first organic solvent at a temperature of less than about 0° C. to form an alkylcarbonyloxy chromanone of Formula (II-C*):

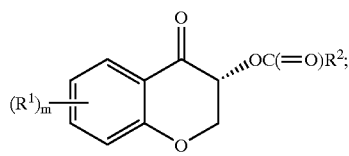
(III*)

and (D) reacting Compound III* with an alkali metal peroxide or hydroperoxide in a second organic solvent at a temperature of less than about 0° C. to form Compound I*.

3. The process according to claim 1, wherein Step C is conducted at a temperature in a range of from about −40 to about 0° C.

4. The process according to claim 1, wherein the first organic solvent is a halogenated hydrocarbon selected from the group consisting of $C_1$–$C_6$ linear and branched halogenated alkanes, $C_2$–$C_6$ linear and branched halogenated alkenes, $C_5$–$C_7$ halogenated cycloalkanes, and $C_6$–$C_{10}$ halogenated aromatic hydrocarbons.

5. The process according to claim 1, wherein $AlCl_3$ is employed in Step C in an amount of at least about 0.1 equivalent per equivalent of Compound II-C.

6. The process according to claim 1, wherein Step D is conducted at a temperature in a range of from about −40 to about 0° C.

7. The process according to claim 1, wherein the second organic solvent is selected from the group consisting of dialkyl ethers wherein each alkyl is independently a $C_1$–$C_6$ alkyl, $C_4$–$C_8$ dialkoxyalkanes, $C_4$–$C_6$ cyclic ethers and diethers, $C_6$–$C_8$ aromatic ethers, and $C_1$–$C_6$ alkyl alcohols.

8. The process according to claim 1, wherein the alkali metal peroxide in Step D is employed in an amount of at least about 1 equivalent per equivalent of Compound III.

9. The process according to claim 1, wherein
each $R^1$ is independently halo, $C_1$–$C_4$ alkyl, halogenated $C_1$–$C_4$ alkyl, $C_1$–$C_4$ alkoxy, or halogenated $C_1$–$C_4$ alkoxy;
$R^2$ is $C_1$–$C_4$ alkyl;
X is chloro or bromo; and
m is an integer from 0 to 2.

10. The process according to claim 1, wherein the alkali metal peroxide or hydroperoxide is lithium peroxide or hydroperoxide.

11. The process according to claim 1, which further comprises:

(B) treating a compound of Formula (II-B):

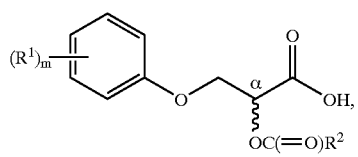
(II-B)

with an acyl halide reagent to form Compound II-C.

12. The process according to claim 11, which further comprises:

(A) treating a compound of Formula (II-A):

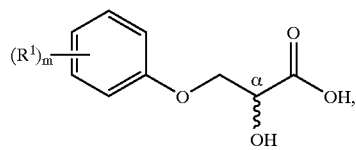
(II-A)

with an acylating agent of Formula (IV):

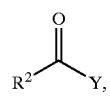
(IV)

in the absence of base, to form Compound II-B; wherein Y is halo.

13. The process according to claim 2, which further comprises:

(B) treating a compound of Formula (II-B*):

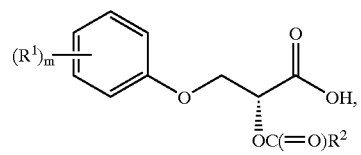
(II-B*)

with an acyl halide reagent to form Compound II-C*.

14. The process according to claim 13, which further comprises:

(A) treating a compound of Formula (II-A*):

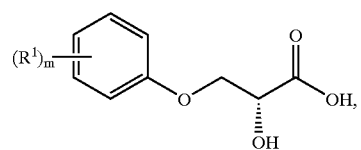
(II-A*)

with an acylating agent of Formula (IV):

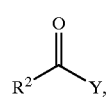
(IV)

in the absence of base, to form Compound II-B*; wherein Y is halo.

15. The process according to claim 1, which further comprises:

(E) treating Compound I with a hydroxylamine of Formula (V):

(V), or an acid salt thereof, to form an oxime of Formula (VI):

(VI)

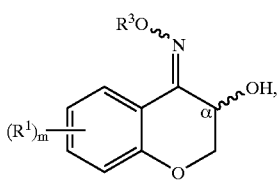

wherein R³ is
(1) hydrogen;
(2) $C_1$–$C_6$ alkyl;
(3) $C_1$–$C_6$ alkyl substituted with one or more substituents, each of which is independently halo, cyano, $C_1$–$C_4$ alkoxy, $C_1$–$C_4$ haloalkoxy, $C_3$–$C_8$ cycloalkyl, or phenyl;
(4) $C_3$–$C_8$ cycloalkyl;
(5) $C_3$–$C_8$ cycloalkyl substituted with one or more substituents, each of which is independently halo, cyano, $C_1$–$C_4$ alkyl, $C_1$–$C_4$ haloalkyl, $C_1$–$C_4$ alkoxy, $C_1$–$C_4$ haloalkoxy, or phenyl;
(6) phenyl; or
(7) phenyl substituted with one or more substituents, each of which is independently $C_1$–$C_4$ alkyl, $C_1$–$C_4$ haloalkyl, $C_1$–$C_4$ alkoxy, $C_1$–$C_4$ haloalkoxy, cyano, or halo.

16. The process according to claim 15, wherein the treating is conducted in an aqueous-polar organic solvent at a temperature in a range of from about 0 to about 40° C.

17. The process according to claim 15, wherein the hydroxylamine V is employed in an amount of at least about 1 equivalent per equivalent of Compound I.

18. The process according to claim 15, which further comprises:
(F) hydrogenating in the presence of a palladium catalyst a mixture comprising Compound VI, a third organic solvent, and HBr to form an aminochromanol of Formula (VII):

(VII)

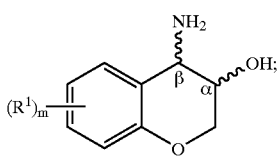

wherein the stereocenters α and β are either both in the R configuration or both in the S configuration.

19. The process according to claim 18, wherein the hydrogenation is conducted at a temperature in the range of from about −20 to about 100° C. and at a pressure of at least about 2 psig (115 kPa).

20. The process according to claim 2, which further comprises:
(E) treating Compound I* with a hydroxylamine of Formula (V):

$H_2N$—$OR^3$ (V), or an acid salt thereof, to form an oxime of Formula (VI*):

(VI*)

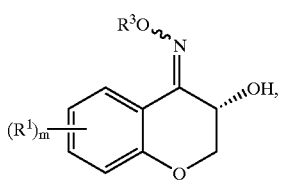

wherein R³ is
(1) hydrogen;
(2) $C_1$–$C_6$ alkyl;
(3) $C_1$–$C_6$ alkyl substituted with one or more substituents, each of which is independently halo, cyano, $C_1$–$C_4$ alkoxy, $C_1$–$C_4$ haloalkoxy, $C_3$–$C_8$ cycloalkyl, or phenyl;
(4) $C_3$–$C_8$ cycloalkyl;
(5) $C_3$–$C_8$ cycloalkyl substituted with one or more substituents, each of which is independently halo, cyano, $C_1$–$C_4$ alkyl, $C_1$–$C_4$ haloalkyl, $C_1$–$C_4$ alkoxy, $C_1$–$C_4$ haloalkoxy, or phenyl;
(6) phenyl; or
(7) phenyl substituted with one or more substituents, each of which is independently $C_1$–$C_4$ alkyl, $C_1$–$C_4$ haloalkyl, $C_1$–$C_4$ alkoxy, $C_1$–$C_4$ haloalkoxy, cyano, or halo.

21. The process according to claim 20, which further comprises:
(F) hydrogenating in the presence of a palladium catalyst a mixture comprising Compound VI*, a third organic solvent, and HBr to form an aminochromanol of Formula (VII*):

(VII*)

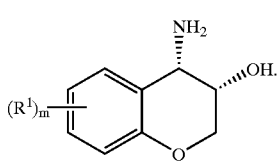

22. A process for preparing hydroxychromanone 6:

6

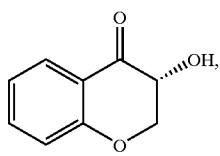

which comprises:
(C) adding acid chloride 4a:

4a

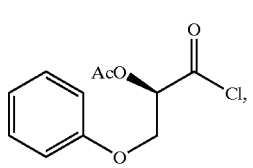

to a solution of $AlCl_3$ in a halogenated hydrocarbon solvent at a temperature of less than about 0° C. to form acetoxy chromanone 5:

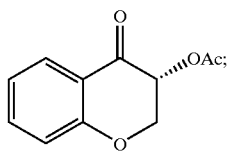

and (D) reacting Compound 5 at a temperature of less than about 0° C. with lithium peroxide or lithium hydroperoxide in an ethereal or alcoholic solvent to form Compound 6.

23. The process according to claim 22, wherein the temperature in Step C is in a range of from about −20 to about 0° C.;

the halogenated hydrocarbon solvent in Step C is a $C_1$–$C_6$ linear or branched halogenated alkane;

$AlCl_3$ is employed in Step C in an amount of from about 0.1 to about 5 equivalents per equivalent of Compound 4a;

the temperature in Step D is in a range of from about −20 to about 0° C.;

the solvent in Step D is selected from the group consisting of dialkyl ethers wherein each alkyl is independently a $C_1$–$C_4$ alkyl, $C_4$–$C_6$ cyclic ethers and diethers, and $C_1$–$C_4$ alkyl alcohols; and the lithium peroxide or hydroperoxide is employed in Step D in an amount of from about 1 to about 5 equivalents per equivalent of Compound 5.

24. The process according to claim 22, which further comprises (E) treating Compound 6 with hydroxylamine or an acid salt thereof to form oxime 7:

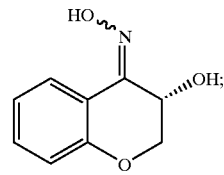

(F) hydrogenating in the presence of a palladium catalyst a mixture comprising Compound 7, an ethereal or alcoholic solvent, and HBr to form aminochromanol 8:

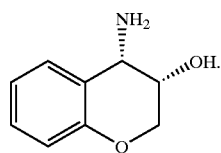

25. The process according to claim 24, wherein the catalyst in Step F is Pd/C;

the amount of HBr in Step F is in the range of from about 0.95 to about 1.05 equivalents per equivalent of 7; and the hydrogenation of Step F is conducted at a temperature in the range of from about −5 to about 5° C.

* * * * *